(12) United States Patent
Goel

(10) Patent No.: US 10,538,799 B2
(45) Date of Patent: Jan. 21, 2020

(54) METHODS AND COMPOSITIONS FOR EXPRESSION OF POLYPEPTIDES IN A CELL

(71) Applicant: Celltheon Corporation, Union City, CA (US)

(72) Inventor: Amita Goel, Union City, CA (US)

(73) Assignee: Celltheon Corporation, Union City, CA (US)

( * ) Notice: Subject to any disclaimer, the term of this patent is extended or adjusted under 35 U.S.C. 154(b) by 0 days.

(21) Appl. No.: 15/730,569

(22) Filed: Oct. 11, 2017

(65) Prior Publication Data
US 2018/0030496 A1 Feb. 1, 2018

Related U.S. Application Data

(63) Continuation of application No. 14/803,813, filed on Jul. 20, 115, now abandoned.

(60) Provisional application No. 62/026,499, filed on Jul. 18, 2014.

(51) Int. Cl.
*C12P 21/02* (2006.01)
*C12N 15/86* (2006.01)

(52) U.S. Cl.
CPC .............. *C12P 21/02* (2013.01); *C12N 15/86* (2013.01); *C12N 2710/16143* (2013.01)

(58) Field of Classification Search
None
See application file for complete search history.

(56) References Cited

U.S. PATENT DOCUMENTS

| 2004/0072352 A1 | 4/2004 | Kim et al. |
| 2007/0128224 A1 | 6/2007 | Van Der Werf et al. |
| 2014/0038233 A1* | 2/2014 | Yoon ..................... C12N 15/85 435/69.1 |
| 2014/0370547 A1 | 12/2014 | Hulesmann et al. |

FOREIGN PATENT DOCUMENTS

| CN | 103525867 | 1/2014 |
| WO | WO 89/01036 | 2/1989 |
| WO | WO 2004/009823 | 1/2004 |

OTHER PUBLICATIONS

Huang et al., Role of the Hepatitis B Virus Posttranscriptional Regulatory Element in Export of Intronless Transcripts; Mol. Cell. Biol., vol. 15, No. 7, p. 3864-3869, 1995.*
International Search Report and Written Opinion for PCT/US2015/041143 dated Jan. 21, 2016 (16 pages).
"Human cytomegalovirus synthetic 5' UTR (reverse compliment) of hCMV-MIE DNA", retrieved from EBI accession No. EM_PAT:A01324, Database accession No. A01324 sequence.
Mariati et al., "Evaluating post-transcriptional regulatory elements for enhancing transient gene expression levels in CHO K1 and HEK293 cells," Protein Expression and Purification, Academic Press, 2010, vol. 69, No. 1, pp. 9-15.
"Vector plasmid p12.4 hCMVp-GFP for CHO cells.", retrieved from EBI accession No. GSN: ADJ57065, Database accession No. ADJ57065 sequence, May 6, 2004.
"Circular plasmid GS vector p12.4 hCMVp-GFP.", retrieved from EBI accession No. DD357297, Database accession No. DD357297 sequence, 2004.

\* cited by examiner

*Primary Examiner* — Addison D Ault
(74) *Attorney, Agent, or Firm* — Sheppard Mullin Richter & Hampton LLP

(57) ABSTRACT

Disclosed herein are vector systems for expression of polypeptides in eukaryotic cells; and methods of obtaining high-level expression of polypeptides in a eukaryotic cell. Methods and compositions for obtaining stable, long-term expression of recombinant polypeptides are also provided.

6 Claims, 10 Drawing Sheets

Specification includes a Sequence Listing.

FIGURE 6

| | | | | | | | | |
|---|---|---|---|---|---|---|---|---|
| pCT 2.1 | RC-dUTR | promoter | uUTR | intron | dUTR | Rtx | poly A | GS | ori/bla |
| pCT 2.36 | RC-dUTR | promoter | uUTR | intron | dUTR | Rtx | poly A | GS | ori/bla |
| pCT 2.39 | RC-dUTR | promoter | uUTR | intron | dUTR | Rtx | poly A | GS | ori/bla |
| pCT 2.51 | RC-dUTR | promoter | uUTR | intron | dUTR | Rtx | poly A | GS | ori/bla |

FIGURE 8

| | | | | | | | | | |
|---|---|---|---|---|---|---|---|---|---|
| LC vector + PRE | RC-dUTR | promoter | uUTR | intron | dUTR | Rtx LC | WPRE | polyA | GS | ori/bla |
| HC vector + PRE | RC-dUTR | promoter | uUTR | intron | dUTR | Rtx HC | WPRE | polyA | GS | ori/bla |
| LC vector - PRE | RC-dUTR | promoter | uUTR | intron | dUTR | Rtx LC | polyA | GS | ori/bla |
| HC vector - PRE | RC-dUTR | promoter | uUTR | intron | dUTR | Rtx HC | polyA | GS | ori/bla |

(+) WPRE Total mini-pools screened by OD (-)WPRE Total mini-pools screened by OD

METHODS AND COMPOSITIONS FOR EXPRESSION OF POLYPEPTIDES IN A CELL

CROSS REFERENCE TO RELATED APPLICATIONS

This application is a continuation of U.S. application Ser. No. 14/803,813, filed Jul. 20, 2015, which claims the benefit of U.S. provisional patent application No. 62/026,499; filed Jul. 18, 2014; the disclosure of which is hereby incorporated by reference, in its entirety, for all purposes.

STATEMENT REGARDING FEDERAL SUPPORT

Not applicable.

FIELD

The present disclosure is in the field of recombinant protein expression.

BACKGROUND

Controlled production of recombinant polypeptides is useful in the fields of research, diagnostics and therapeutics. For example, purified recombinant proteins can be used as therapeutics, for screening, for lead optimization and for target validation. Typical expression systems are characterized by a host cell line comprising an expression vector containing a heterologous promoter operatively linked to a cDNA encoding a gene product of interest. See, for example, U.S. Pat. Nos. 5,168,062 and 5,385,839. Additional methods for protein production involve integration of promoters or other regulatory sequences into a chromosome adjacent to a gene whose expression is to be regulated. See, e.g., U.S. Pat. Nos. 5,272,071; 5,641,670; 5,733,761; 5,968,502 and 6,361,972.

Expression systems which yield levels of protein that are higher than those obtained using presently available systems are desirable.

SUMMARY

Disclosed herein are new methods for expression of polypeptides in cells that utilize new nucleic acid vectors, also disclosed herein. The vectors include transcriptional regulatory sequences derived from viral genomes, such as the cytomegalovirus (CMV) genome. In some embodiments, the expression vectors further include a post-transcriptional regulatory element (PRE). In some embodiments, the expression vectors further include a MAR/SAR sequence. These vectors provide higher expression levels of genes to which they are operatively linked, thus providing higher expression of recombinant proteins, compared to existing recombinant expression systems.

In addition, the vectors disclosed herein provide stable, high-level expression of recombinant polypeptides for up to 50 or more generations, thereby exceeding the expression longevity of currently-existing expression systems.

Thus, the present disclosure provides, inter alia, the following embodiments.
1. A polynucleotide comprising:
  (a) a cytomegalovirus (CMV) RC-UTR downstream sequence,
  (b) a CMV major immediate early (MIE) promoter,
  (c) a CMV UTR upstream sequence,
  (d) a CMV Intron A, and
  (e) a CMV UTR downstream sequence.
2. The polynucleotide of embodiment 1, wherein the cytomegalovirus is human cytomegalovirus (hCMV).
3. The polynucleotide of embodiment 1, wherein the polynucleotide comprises the nucleotide sequence of SEQ ID NO: 1 or a nucleotide sequence that is substantially identical to SEQ ID NO:1.
4. A polynucleotide having at least 80%, 85%, 90%, 95%, 98%, or 99% sequence identity to the polynucleotide of embodiment 3.
5. A polynucleotide that is complementary to the polynucleotide of embodiment 3.
6. A polynucleotide that hybridizes under stringent conditions to the polynucleotide of embodiment 3.
7. A nucleic acid vector comprising the polynucleotide of embodiment 1.
8. The vector of embodiment 7, wherein elements (a)-(e) of the CMV sequences are present in upstream-to-downstream order.
9. The vector of embodiment 7, further comprising a polyadenylation signal.
10. The vector of embodiment 9, wherein the polyadenylation signal is selected from the group consisting of the simian virus 40 (SV40) polyadenylation signal and the bovine growth hormone (BGH) polyadenylation signal.
11. The vector of embodiment 9, further comprising a multiple cloning site disposed between the CMV sequences and the polyadenylation signal.
12. The vector of embodiment 9, further comprising a transgene.
13. The vector of embodiment 12, further comprising a post-transcriptional element (PRE).
14. The vector of embodiment 13, wherein the PRE is selected from the group consisting of a woodchuck hepatitis virus PRE (WPRE), a human hepatitis B virus PRE (HPRE), and hybrids thereof.
15. The vector of embodiment 12, further comprising a MAR/SAR sequence.
16. The vector of embodiment 15, wherein the MAR/SAR sequence is selected from the group consisting of a chicken lysozyme MAR/SAR (CLM) sequence, an interferon alpha-2 MAR/SAR (IAM) sequence, an interferon beta MAR/SAR (IBM) sequence, a X29 MAR/SAR sequence, a S4 MAR/SAR sequence and hybrids thereof
17. The vector of embodiment 11, further comprising:
  (a) sequences encoding a first selection marker that functions in eukaryotic cells to provide resistance to a first selective agent;
  (b) a promoter operably linked to the sequences encoding the first selection marker; and
  (c) a second polyadenylation signal operably linked to the sequences encoding the first selection marker.
18. The vector of embodiment 17, wherein the first selection marker is selected from the group consisting of genes encoding dihydrofolate reductase (DHFR), glutamine synthetase (GS), puromycin-N-acetyl transferase, hygromycin phosphotransferase, aminoglycoside-3-phosphotransferase, ble, and neomycin resistance.
19. The vector of embodiment 17, wherein the first selective agent is selected from the group consisting of methotrexate, neomycin, geneticin, puromycin, bleomycin, Zeocin, blasticidin, hygromycin, methionine sulfoximine and L-glutamine.
20. The vector of embodiment 17, wherein the promoter is selected from the group consisting of the cytomegalovirus (CMV) major immediate early (MIE) promoter, the herpes simplex virus thymidine kinase (TK) promoter, the SV40 early promoter, the SV40 late promoter, the Ubiquitin C promoter, the phosphoglycerate kinase (PGK) promoter and the eukaryotic elongation factor-1 alpha (EF-1α) promoter.

21. The vector of embodiment 17, wherein the second polyadenylation signal is selected from the group consisting of the SV40 polyadenylation signal and the bovine growth hormone (BGH) polyadenylation signal.

22. The vector of embodiment 7 further comprising:
   (a) a replication origin that functions in prokaryotic cells; and
   (b) a second selection marker that functions in prokaryotic cells to confer resistance to a second selective agent.

23. The vector of embodiment 22, wherein the replication origin is selected from the group consisting of the pBR322 origin (rep), oriC, the pSC101 origin and the pUC origin.

24. The vector of embodiment 22, wherein the second selection marker is a gene encoding beta-lactamase.

25. The vector of embodiment 22, wherein the second selective agent is selected from the group consisting of ampicillin, kanamycin, chloramphenicol and tetracycline.

26. The vector of embodiment 12, further comprising a second transgene.

27. The vector of embodiment 26, wherein the second transgene is in operative linkage with a second promoter and a third polyadenylation signal.

28. The vector of embodiment 27, wherein the second promoter is selected from the group consisting of SEQ ID NO:1, homologues of SEQ ID NO:1, functional equivalents of SEQ ID NO:1, the cytomegalovirus (CMV) major immediate early (MIE) promoter, the herpes simplex virus thymidine kinase (TK) promoter, the SV40 early promoter, the SV40 late promoter, the Ubiquitin C promoter, the phosphoglycerate kinase (PGK) promoter and the eukaryotic elongation factor-1 alpha (EF-1α) promoter 29. The vector of embodiment 27, wherein the third polyadenylation signal is selected from the group consisting of the SV40 polyadenylation signal and the bovine growth hormone (BGH) polyadenylation signal.

30. The vector of embodiment 26, further comprising an internal ribosome entry site (IRES) disposed between the first transgene and the second transgene.

31. The vector of embodiment 30, wherein the IRES is a picornaviral IRES, an encephalomyocarditis virus (EMCV) IRES, a Chenyl IRES or IRES2A.

32. The vector of embodiment 12, wherein the transgene is a gene that encodes a protein selected from the group consisting a recombinant protein, a fusion protein, an antibody, a cytokine, a hormone, an enzyme and a clotting factor.

33. The vector of embodiment 32, wherein the antibody is a monoclonal antibody, a single chain antibody, a bispecific antibody or an antibody conjugate.

34. The vector of embodiment 33, wherein the antibody is selected from the group consisting of anti-CD20 (Rituximab), anti-CD25 (Daclizumab, Basiliximab), anti-p18Her-2 (Trastuzumab), anti-TNFα (Infliximab, Adalimumab), anti-pF-RSV (Palivizumab), anti-CD52 (Alemtuzumab), anti-IgE-Fc (Omalizumab), anti-erbB1 (Cetuximab), anti-Complement C5 (Eculizumab), anti-alpha 4 integrin (Natalizumab), anti-CDE33 (Gemtuzumab), anti-CTLA-4 (Ipilimumab), anti-HuMax-CD20 (Ofatumumab), anti- ABX-Epidermal Growth Factor (Panitumumab), anti-MK-3475 (Pembrolizumab), and conjugates thereof.

35. The vector of embodiment 32, wherein the cytokine is erythropoietin, granulocyte colony-stimulating factor (G-CSF), filgrastim, or PEGfilgrastim.

36. The vector of embodiment 32, wherein the hormone is human growth hormone, luteinizing hormone (Luveris), or epoetin (Procrit).

37. The vector of embodiment 32, wherein the enzyme is selected from the group consisting of alpha-glucosidase (Myozyme), Laronidase (Aldurazyme), IgG-CTLA4 fusion (Orencia), and N-acetylgactosameine 4-Sulfatase (Nagdazyme).

38. The vector of embodiment 26, wherein the first and second transgenes are an antibody heavy chain and an antibody light chain.

39. A virus comprising the vector of embodiment 7.

40. The vector of embodiment 7, wherein the vector is a plasmid or a cosmid.

41. A cell comprising the vector of embodiment 12, wherein the cell is selected from the group consisting of a prokaryotic cell and a eukaryotic cell.

42. The cell of embodiment 41, wherein the eukaryotic cell is selected from the group consisting of a plant cell, an insect cell, a fungal cell and a mammalian cell.

43. The cell of embodiment 42, wherein the eukaryotic cell is a mammalian cell.

44. The cell of embodiment 43, wherein the cell is selected from the group consisting of CHO, CHOK1, NS0, HEK293, BHK, SP20, PERC.6, CAP®, CAP-T® and derivatives thereof.

45. The cell of embodiment 43, wherein the cell is a myeloma or a hybridoma or a derivative thereof.

46. The cell of embodiment 43, wherein the cell has been adapted to grow in serum-free medium.

47. The cell of embodiment 41, wherein the cell is *E. coli*.

48. A method for expressing a polypeptide in a cell, the method comprising:
   (a) introducing the vector of embodiment 12 into a cell; and
   (b) culturing the cell under conditions such that the vector is stably maintained in the cell.

49. The method of embodiment 48, wherein the cell is selected from the group consisting of CHO, CHOK1, NS0, HEK293, BHK, SP20, PERC.6, CAP®, CAP-T® and derivatives thereof.

50. The method of embodiment 48, wherein the cell is a myeloma or a hybridoma or a derivative thereof.

51. The method of embodiment 48, wherein the cell is cultured in serum-containing medium.

52. The method of embodiment 48, wherein the cell is cultured in serum-free medium.

53. The method of embodiment 52, wherein the cell is pre-adapted for growth in serum-free medium prior to introducing the vector into the cell.

54. A method for expressing a polypeptide in a population of transfected cells, the method comprising:
   transfecting a population of cells with the vector of embodiment 13;
   wherein greater than 20% of the cells in the population express the polypeptide.

55. The method of embodiment 54, wherein greater than 40% of the cells in the population express the polypeptide.

56. The method of embodiment 54, further wherein the cells expressing the polypeptide express the polypeptide for at least ten generations after selection.

57. The method of embodiment 54, wherein the cells expressing the polypeptide express the polypeptide for at least twenty-five generations after selection.

58. The method of embodiment 54, wherein the cells expressing the polypeptide express the polypeptide for at least fifty generations after selection.

59. A polynucleotide comprising any one of SEQ ID NOs: 2, 3 4 or 6, a sequence substantially identical to any one of SEQ ID NOs: 2, 3 4 or 6, or any combination thereof.

BRIEF DESCRIPTION OF THE DRAWINGS

FIG. 6 shows schematic diagrams of vectors used to test the activity of various transcription control elements. The vectors did not contain a PRE. The name of the plasmid is shown to the left of each schematic. Regions that were deleted in each of the plasmids are indicated by strikethrough (e.g., a vector diagram in which the intron portion is shown in strikethrough indicates that that vector lacks the intron).

Nomenclature is as follows. RC-dUTR: reverse complement of downstream portion of CMV MIE 5' untranslated region sequence (SEQ ID NO:2); promoter: CMV MIE promoter enhancer sequence (SEQ ID NO:3); uUTR: upstream portion of CMV MIE 5' untranslated region sequence (SEQ ID NO:4); intron: CMV MIE Intron A (SEQ ID NO: 5); dUTR: downstream portion of CMV MIE 5' untranslated region sequence (SEQ ID NO:6); Rtx: sequences encoding Rituximab light chain; poly A: bGH polyadenylation signal; GS: expression cassette containing promoter, polyadenylation signal and sequences encoding glutamine synthase disposed therebetween; ori: prokaryotic replication origin; bla: sequences encoding fβ-lactamase.

Figure 7:
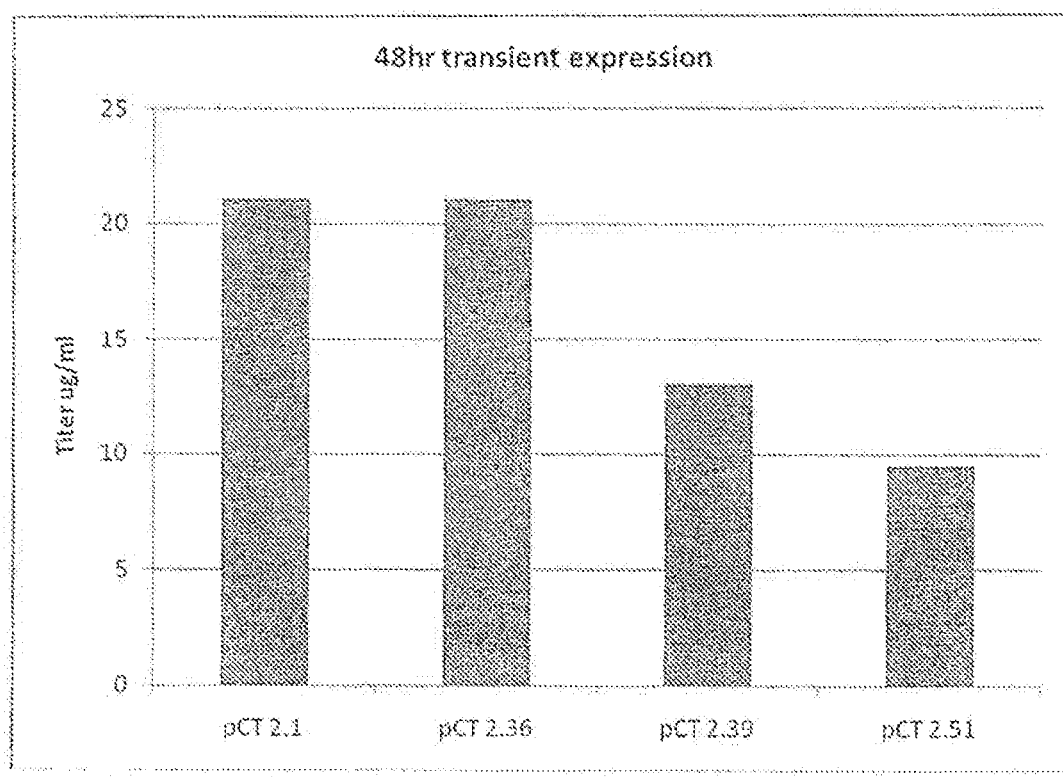

FIG. 7 shows Rtx levels in cells transfected with the vectors shown in FIG. 6.

FIG. 8 shows schematic diagrams of vectors used to test the effect of a PRE on expression levels and stability of expression. Nomenclature is the same as in FIG. 6 with the addition that "Rtx LC" refers to sequences encoding Rituximab light chain, "Rtx HC" refers to sequences encoding Rituximab heavy chain, and "WPRE" refers to the woodchuck hepatitis virus post-transcriptional regulatory element.

Figure 9:
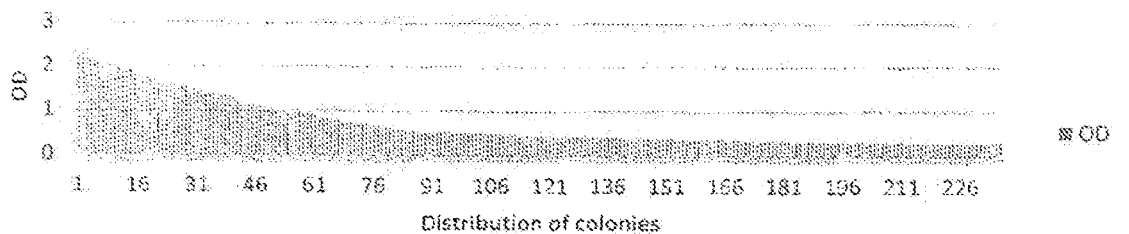

FIG. 9 shows analysis of Rtx expression (by ELISA) in mini-pools from a population of CHO cells transfected with Rtx-LC and Rtx-HC-expressing vectors in which the vectors contained a PRE. Bars represent Rtx levels, expressed as optical density (OD) obtained from an ELISA assay.

Figure 10:
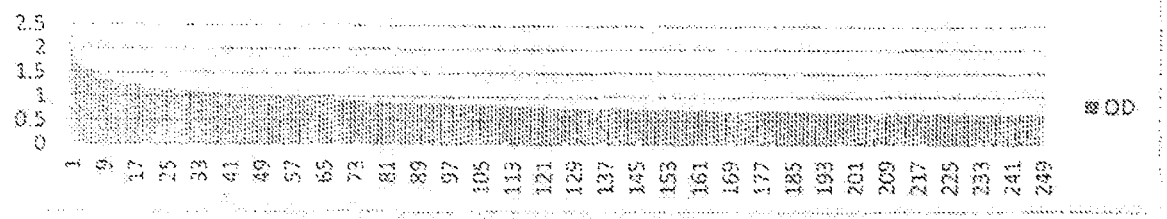

FIG. 10 shows analysis of Rtx expression (by ELISA) in mini-pools from a population of CHO cells transfected with Rtx-LC and Rtx-HC-expressing vectors in which the vectors did not contain a PRE. Bars represent Rtx levels, expressed as optical density (OD) obtained from an ELISA assay.

Figure 11:
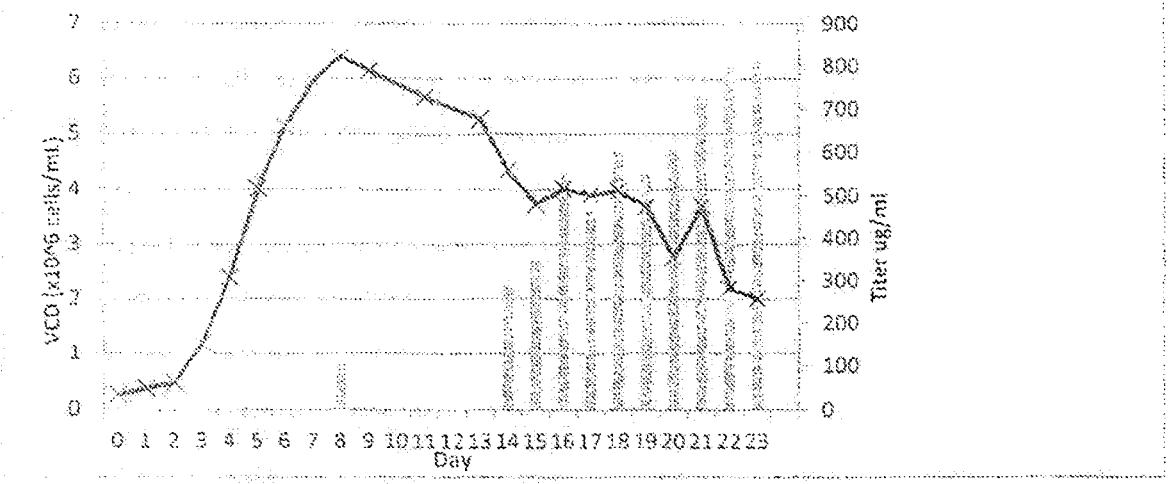

FIG. 11 shows high level expression of Rtx in a fed-batch culture of a selected mini-pool from a population of CHO cells transfected with Rtx-LC and Rtx-HC-expressing vectors in which the vectors contained a PRE. The trace connecting data points indicated by "X" shows viable cell density (VCD); bars indicate Rtx concentration (obtained by converting OD values obtained from ELISA assay to concentration using a Rtx standard curve).

Figure 12:
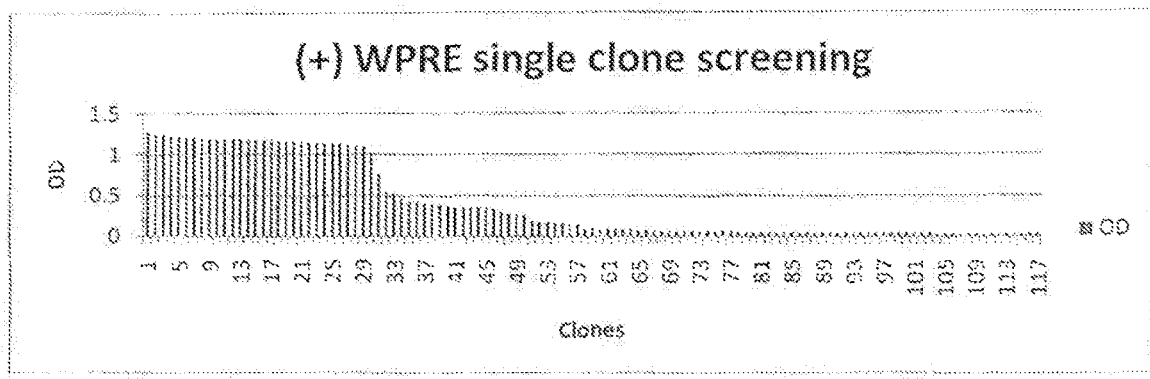

FIG. 12 shows analysis of Rtx expression in clones from a population of CHO cells transfected with Rtx-LC and Rtx-HC-expressing vectors in which the vectors contained a PRE. Bars represent Rtx levels, expressed as optical density (OD) obtained from an ELISA assay.

Figure 13:
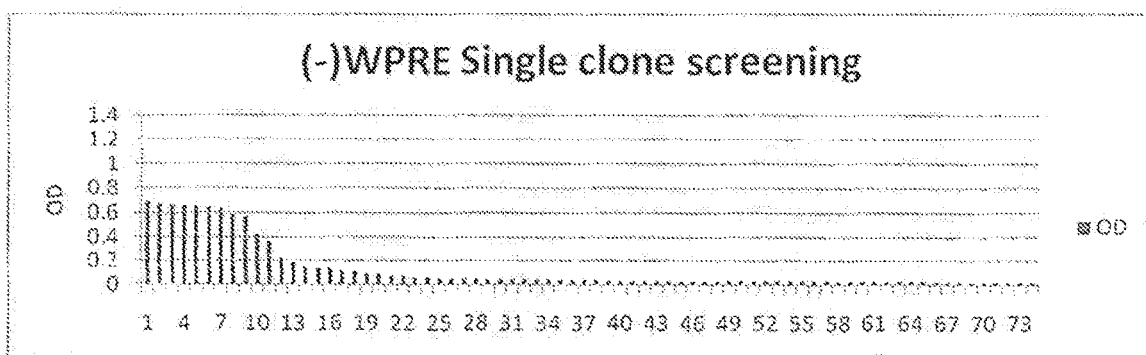

FIG. 13 shows analysis of Rtx expression in clones from a population of CHO cells transfected with Rtx-LC and Rtx-HC-expressing vectors in which the vectors did not contain a PRE. Bars represent Rtx levels, expressed as optical density (OD) obtained from an ELISA assay.

Figure 14:
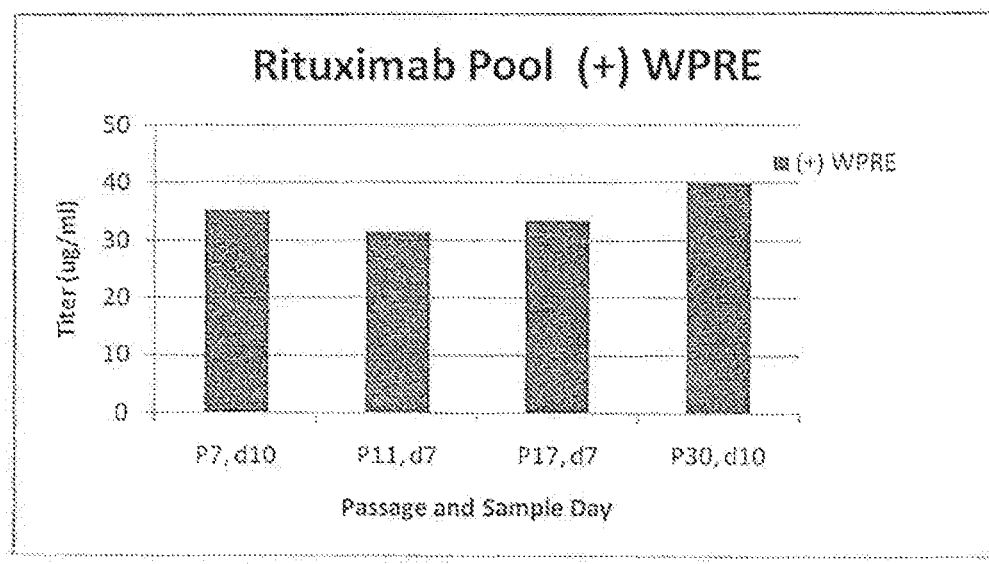

FIG. 14 shows results of ELISA assays of a pool obtained from cells that had been transfected with Rtx-expressing vectors containing a PRE. "P" refers to number of passages following selection, and "d" refers to the number of days cells were in batch culture after they were removed from the particular passage. For example, P7, d10 indicates that cells were removed at the seventh passage and cultured in batch mode for ten days prior to ELISA assay for Rtx.

Figure 15:
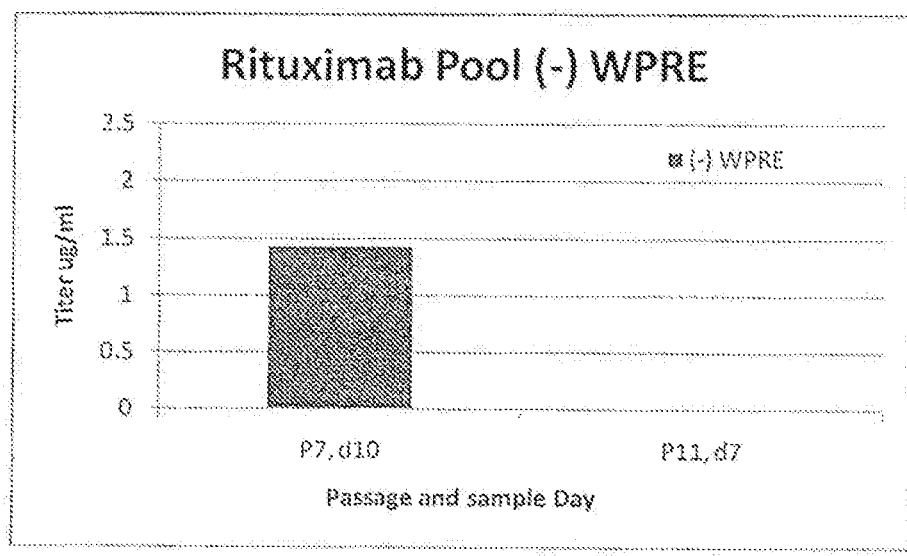

FIG. 15 shows results of ELISA assays of a pool obtained from cells that had been transfected with Rtx-expressing vectors lacking a PRE. Nomenclature is the same as in FIG. 14.

Figure 16:
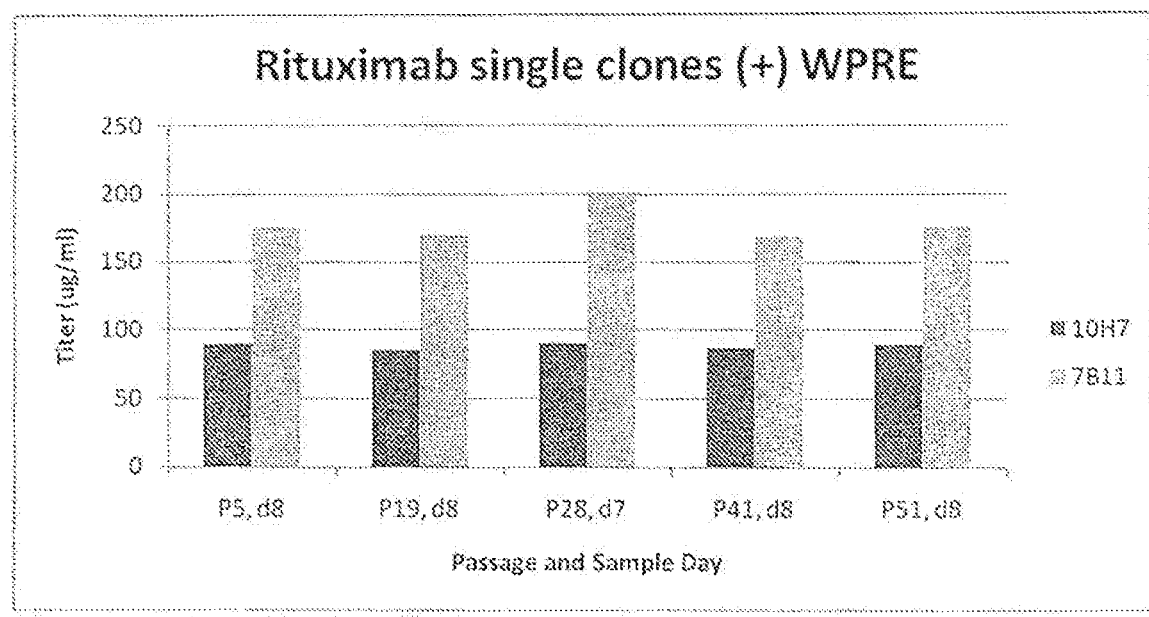

FIG. 16 shows results of ELISA assays of two clones (10H7, black bars; and 7B11, gray bars) obtained from cells that had been transfected with Rtx-expressing vectors containing a PRE. Nomenclature is the same as in FIG. 14.

DETAILED DESCRIPTION

Practice of the present disclosure employs, unless otherwise indicated, standard methods and conventional techniques in the fields of cell biology, molecular biology, biochemistry, cell culture, immunology, oncology, recombinant DNA and related fields as are within the skill of the art. Such techniques are described in the literature and thereby available to those of skill in the art. See, for example, Alberts, B. et al., "Molecular Biology of the Cell," 5th edition, Garland Science, New York, N.Y., 2008; Voet, D. et al. "Fundamentals of Biochemistry: Life at the Molecular Level," 3rd edition, John Wiley & Sons, Hoboken, N.J., 2008; Sambrook, J. et al., "Molecular Cloning: A Laboratory Manual," 3rd edition, Cold Spring Harbor Laboratory Press, 2001; Ausubel, F. et al., "Current Protocols in Molecular Biology," John Wiley & Sons, New York, 1987 and periodic updates; Freshney, R. I., "Culture of Animal Cells: A Manual of Basic Technique," 4th edition, John Wiley & Sons, Somerset, N.J., 2000; and the series "Methods in Enzymology," Academic Press, San Diego, Calif.

Transcriptional Regulatory Sequences

The present disclosure provides nucleotide sequences, along with polynucleotides and vectors comprising said sequences, useful for expressing recombinant polypeptides in eukaryotic cells (e.g., mammalian cells) and methods for using said sequences. The sequences comprise one or more transcriptional control regions (i.e., transcriptional regulatory sequences) using elements present in viral genomes.

Elements from various viral genomes are suitable for use in the present technology. Non-limiting examples include those from retrovirus, adenovirus, adeno-associated virus, and alphavirus. For instance, examples of viral promoters include the cytomegalovirus (CMV) promoter, simian virus 40 (SV40) promoter, Rous sarcoma virus long terminal repeat (RSV-LTR), Moloney murine leukemia virus (MoMLV) LTR, and other retroviral LTR promoters.

In one embodiment, a polynucleotide or vector of the present disclosure includes one, or more or all of the following elements: (a) a viral reverse complement of the downstream UTR (RC-dUTR) downstream sequence, (b) a viral promoter, (c) a viral untranslated region (UTR) upstream sequence, (d) a viral Intron A, and (e) a viral UTR downstream sequence.

In one embodiment, the polynucleotide or vector of the present disclosure includes at least two of such elements, such as, (b) and (c), (b) and (d), (b) and (e), (a) and (b), (c) and (d), (c) and (e), or (d) and (e).

In one embodiment, the polynucleotide or vector of the present disclosure includes at least three of such elements, such as, (b), (c) and (d); (b), (c) and (e); (b), (d) and (e); (a), (b), and (c), (a), (b) and (d), (a), (b), and (e); (a), (c) and (e); (a), (c) and (d), and (a), (d) and (e).

In one embodiment, the polynucleotide or vector of the present disclosure includes at least four of such elements, such as, (a), (b), (c) and (d); (a), (b), (c) and (e); (a), (b), (d) and (e); (a), (c), (d) and (e); and (b), (c), (d) and (e).

In some embodiments, the elements are derived from cytomegalovirus (CMV) such as the CMV transcriptional regulatory regions including the CMV major immediate early (MIE) promoter. The CMV MIE promoter contains the following elements: (a) promoter/enhancer sequences, (b) a 5' untranslated region (UTR), and (c) an intron. The intron is located within the UTR, dividing the UTR into a UTR upstream (uUTR) sequence and a UTR downstream (dUTR) sequence. In the vectors disclosed herein, the transcriptional control region contains, in addition to promoter/enhancer, UTR and intron; a segment corresponding to the UTR downstream sequence that is present upstream of the promoter/enhancer sequences in reverse orientation. This segment is denoted the reverse complement of the downstream UTR (RC-dUTR). In one embodiment, the transcriptional control region of the vectors can be described schematically as follows: RC-dUTR/promoter/uUTR/intron/dUTR. An exemplary sequence of this particular transcriptional control region is:

(SEQ ID NO: 1)
GTGTCAAGGACGGTGACTGCAGTGAATAATAAAATGTGTGTTTGTCCGAAA

TACGCGTTTTGAGATTTCTGTCGCCGACTAAATTCATGTCGCGCGATAGTG

GTGTTTATCGCCGATAGAGATGGCGATATTGGAAAAATCGATATTTGAAAA

TATGGCATATTGAAAATGTCGCCGATGTGAGTTTCTGTGTAACTGATATCG

CCATTTTTCCAAAAGTGATTTTTGGGCATACGCGATATCTGGCGATAGCGG

CTTATATCGTTTACGGGGATGGCGATAGACGACTTTGGTGACTTGGGCGA

TTCTGTGTGTCGCAAATATCGCAGTTTCGATATAGGTGACAGACGATATGA

GGCTATATCGCCGATAGAGGCGACATCAAGCTGGCACATGGCCAATGCATA

TCGATCTATACATTGAATCAATATTGGCCATTAGCCATATTATTCATTGGT

TATATAGCATAAATCAATATTGGCTATTGGCCATTGCATACGTTGTATCCA

TATCATAATATGTACATTTATATTGGCTCATGTCCAACATTACCGCCATGT

TGACATTGATTATTGACTAGTTATTAATAGTAATCAATTACGGGGTCATTA

GTTCATAGCCCATATATGGAGTTCCGCGTTACATAACTTACGGTAAATGGC

CCGCCTGGCTGACCGCCCAACGACCCCCGCCCATTGACGTCAATAATGACG

TATGTTCCCATAGTAACGCCAATAGGGACTTTCCATTGACGTCAATGGGTG

GAGTATTTACGGTAAACTGCCCACTTGGCAGTACATCAAGTGTATCATATG

CCAAGTACGCCCCCTATTGACGTCAATGACGGTAAATGGCCCGCCTGGCAT

TATGCCCAGTACATGACCTTATGGGACTTTCCTACTTGGCAGTACATCTAC

GTATTAGTCATCGCTATTACCATGGTGATGCGGTTTTGGCAGTACATCAAT

GGGCGTGGATAGCGGTTTGACTCACGGGGATTTCCAAGTCTCCACCCCATT

GACGTCAATGGGAGTTTGTTTTGGCACCAAAATCAACGGGACTTTCCAAAA

TGTCGTAACAACTCCGCCCCATTGACGCAAATGGGCGGTAGGCGTGTACGG

TGGGAGGTCTATATAAGCAGAGCTCGTTTAGTGAACCGTCAGATCGCCTGG

AGACGCCATCCACGCTGTTTTGACCTCCATAGAAGACACCGGGACCGATCC

AGCCTCCGCGGCCGGGAACGGTGCATTGGAACGCGGATTCCCCGTGCCAAG

AGTGACGTAAGTACCGCCTATAGAGTCTATAGGCCCACCCCCTTGGCTTCT

TATGCATGCTATACTGTTTTTGGCTTGGGGTCTATACACCCCCGCTTCCTC

ATGTTATAGGTGATGGTATAGCTTAGCCTATAGGTGTGGGTTATTGACCAT

-continued
```
TATTGACCACTCCCCTATTGGTGACGATACTTTCCATTACTAATCCATAAC

ATGGCTCTTTGCCACAACTCTCTTTATTGGCTATATGCCAATACACTGTCC

TTCAGAGACTGACACGGACTCTGTATTTTTACAGGATGGGGTCTCATTTAT

TATTTACAAATTCACATATACAACACCACCGTCCCCAGTGCCCGCAGTTTT

TATTAAACATAACGTGGGATCTCCACGCGAATCTCGGGTACGTGTTCCGGA

CATGGGCTCTTCTCCGGTAGCGGCGGAGCTTCTACATCCGAGCCCTGCTCC

CATGCCTCCAGCGACTCATGGTCGCTCGGCAGCTCCTTGCTCCTAACAGTG

GAGGCCAGACTTAGGCACAGCACGATGCCCACCACCACCAGTGTGCCGCAC

AAGGCCGTGGCGGTAGGGTATGTGTCTGAAAATGAGCTCGGGGAGCGGGCT

TGCACCGCTGACGCATTTGGAAGACTTAAGGCAGCGGCAGAAGAAGATGCA

GGCAGCTGAGTTGTTGTGTTCTGATAAGAGTCAGAGGTAACTCCCGTTGCG

GTGCTGTTAACGGTGGAGGGCAGTGTAGTCTGAGCAGTACTCGTTGCTGCC

GCGCGCGCCACCAGACATAATAGCTGACAGACTAACAGACTGTTCCTTTCC

ATGGGTCTTTTCTGCAGTCACCGTCCTTGACACG
```

In the sequence shown above, underlined portions represents UTR sequences. The first underlined portion is the RC-dUTR; the underlined portion in the middle of the sequence represents the uUTR; and the underlined portion at the end of the sequence represents the dUTR. Sequences between the RC-dUTR and the uUTR represent the promoter/enhancer; and sequences between the uUTR and the dUTR represent the intron (Intron A).

(SEQ ID NO: 2)
An exemplary RC-dUTR sequence is GTGTCAAGGACGGTGA.

An exemplary promoter/enhancer sequence is:

(SEQ ID NO: 3)
```
CTGCAGTGAATAATAAAATGTGTGTTTGTCCGAAATACGCGTTTTGAGATT

TCTGTCGCCGACTAAATTCATGTCGCGCGATAGTGGTGTTTATCGCCGATA

GAGATGGCGATATTGGAAAAATCGATATTTGAAAATATGGCATATTGAAAA

TGTCGCCGATGTGAGTTTCTGTGTAACTGATATCGCCATTTTTCCAAAAGT

GATTTTTGGGCATACGCGTATCTGGCGATAGCGGCTTATATCGTTTACGG

GGGATGGCGATAGACGACTTTGGTGACTTGGGCGATTCTGTGTGTCGCAAA

TATCGCAGTTTCGATATAGGTGACAGACGATATGAGGCTATATCGCCGATA

GAGGCGACATCAAGCTGGCACATGGCCAATGCATATCGATCTATACATTGA

ATCAATATTGGCCATTAGCCATATTATTCATTGGTTATATAGCATAAATCA

ATATTGGCTATTGGCCATTGCATACGTTGTATCCATATCATAATATGTACA

TTTATATTGGCTCATGTCCAACATTACCGCCATGTTGACATTGATTATTGA

CTAGTTATTAATAGTAATCAATTACGGGGTCATTAGTTCATAGCCCATATA

TGGAGTTCCGCGTTACATAACTTACGGTAAATGGCCCGCCTGGCTGACCGC

CCAACGACCCCCGCCCATTGACGTCAATAATGACGTATGTTCCCATAGTAA

CGCCAATAGGGACTTTCCATTGACGTCAATGGGTGGAGTATTTACGGTAAA

CTGCCCACTTGGCAGTACATCAAGTGTATCATATGCCAAGTACGCCCCCTA

TTGACGTCAATGACGGTAAATGGCCCGCCTGGCATTATGCCCAGTACATGA

CCTTATGGGACTTTCCTACTTGGCAGTACATCTACGTATTAGTCATCGCTA

TTACCATGGTGATGCGGTTTTGGCAGTACATCAATGGGCGTGGATAGCGGT

TTGACTCACGGGGATTTCCAAGTCTCCACCCCATTGACGTCAATGGGAGTT

TGTTTTGGCACCAAAATCAACGGGACTTTCCAAAATGTCGTAACAACTCCG

CCCCATTGACGCAAATGGGCGGTAGGCGTGTACGGTGGGAGGTCTATATAA

GCAGAGCTCGTTTAGTGAACCG
```

An exemplary upstream UTR (uUTR) sequence is:
(SEQ ID NO: 4)
```
TCAGATCGCCTGGAGACGCCATCCACGCTGTTTTGACCTCCATAGAAGACA

CCGGGACCGATCCAGCCTCCGCGGCCGGGAACGGTGCATTGGAACGCGGAT

TCCCCGTGCCAAGAGTGAC
```

An exemplary intron sequence is:
(SEQ ID NO: 5)
```
GTAAGTACCGCCTATAGAGTCTATAGGCCCACCCCCTTGGCTTCTTATGCA

TGCTATACTGTTTTTGGCTTGGGGTCTATACACCCCCGCTTCCTCATGTTA

TAGGTGATGGTATAGCTTAGCCTATAGGTGTGGGTTATTGACCATTATTGA

CCACTCCCCTATTGGTGACGATACTTTCCATTACTAATCCATAACATGGCT

CTTTGCCACAACTCTCTTTATTGGCTATATGCCAATACACTGTCCTTCAGA

GACTGACACGGACTCTGTATTTTTACAGGATGGGGTCTCATTTATTATTTA

CAAATTCACATATACAACACCACCGTCCCCAGTGCCCGCAGTTTTTATTAA

ACATAACGTGGGATCTCCACGCGAATCTCGGGTACGTGTTCCGGACATGGG

CTCTTCTCCGGTAGCGGCGGAGCTTCTACATCCGAGCCCTGCTCCCATGCC

TCCAGCGACTCATGGTCGCTCGGCAGCTCCTTGCTCCTAACAGTGGAGGCC

AGACTTAGGCACAGCACGATGCCCACCACCACCAGTGTGCCGCACAAGGCC

GTGGCGGTAGGGTATGTGTCTGAAAATGAGCTCGGGGAGCGGGCTTGCACC

GCTGACGCATTTGGAAGACTTAAGGCAGCGGCAGAAGAAGATGCAGGCAGC

TGAGTTGTTGTGTTCTGATAAGAGTCAGAGGTAACTCCCGTTGCGGTGCTG

TTAACGGTGGAGGGCAGTGTAGTCTGAGCAGTACTCGTTGCTGCCGCGCGC

GCCACCAGACATAATAGCTGACAGACTAACAGACTGTTCCTTTCCATGGGT

CTTTTCTGCAG
```

(SEQ ID NO: 6)
An exemplary downstream UTR (dUTR) sequence is TCACCGTCCTTGACACG.

Accordingly, disclosed herein are polynucleotides comprising any of SEQ ID NOs:1-6, polynucleotides complementary to any of SEQ ID NOs:1-6, polynucleotides that hybridize to any of SEQ ID NOs:1-6 under stringent conditions, and polynucleotides having homology to any of SEQ ID NOs:1-6. Homologous polynucleotides can have 50% or greater sequence identity, 60% or greater sequence identity, 70% or greater sequence identity, 75% or greater sequence identity, 80% or greater sequence identity, 90% or greater sequence identity, 95% or greater sequence identity, 98% or greater sequence identity, or 99% or greater sequence identity, to any of SEQ ID NOs:1-6.

Functional equivalents to any of SEQ ID NOs 1-6 are also provided. A functional equivalent is a sequence that is not identical to a reference sequence, but performs the same function, e.g., promotion of transcription or increase in frequency of transcription initiation. A sequence that is functionally equivalent to a reference sequence can be homologous to, or substantially identical to, the reference sequence.

In additional embodiments, any one of SEQ ID NOs: 2-6, or sequences that are homologous, complementary, functionally equivalent, or substantially identical to any of SEQ ID NOs: 2-6, or any combinations thereof, can be used as a transcriptional regulatory element in the vectors disclosed herein.

Vectors

Also disclosed are vectors comprising a transcriptional control region as exemplified by any of SEQ ID NOs:1-6. Sequences corresponding to the MIE of any cytomegalovirus (e.g., human, mouse, hamster and/or hybrids and chimeras thereof) can be used in the vectors disclosed herein. In addition, homologues and functional equivalents of SEQ ID NOs 1-6, as described elsewhere herein, are also contemplated for use in the methods and compositions disclosed herein.

In addition to the transcriptional control region, the vectors optionally contain a "gene of interest" or "transgene" in operative linkage with the transcriptional control region. Generally, the transcriptional control region will be present upstream, in the transcriptional sense, of the transgene. Vectors containing a transgene can be used for in vitro expression of one or more polypeptides encoded by the transgene(s). Vectors can comprise one transgene, two transgenes or more than two transgenes.

A transgene can encode, for example, a recombinant protein, a fusion protein, an antibody, a cytokine, a hormone, an enzyme and a clotting factor. Exemplary antibodies include monoclonal antibodies, single chain antibodies, bispecific antibodies, and antibody conjugates.

Exemplary transgenes include those encoding therapeutic proteins, e.g., hormones (such as, for example, growth hormone), cytokines (e.g., erythropoietin), antibodies, monoclonal antibodies (e.g., rituximab), antibody conjugates, fusion proteins (e.g., IgG-fusion proteins), interleukins, CD proteins, MHC proteins, enzymes and clotting factors. Antibody heavy chains and antibody light chains can be expressed from separate vectors, or from the same vector containing two expression cassettes.

Exemplary antibodies include, but are not limited to, therapeutic antibodies such as, for example, anti-CD20 (Rituximab), anti-CD25 (Daclizumab, Basiliximab), anti-p18Her-2 (Trastuzumab), anti-TNFα (Infliximab, Adalimumab), anti-pF-RSV (Palivizumab), anti-CD52 (Alemtuzumab), anti-IgE-Fc (Omalizumab), anti-erbB1 (Cetuximab), anti-Complement C5 (Eculizumab), anti-alpha 4 integrin (Natalizumab), anti-CDE33 (Gemtuzumab), anti-CTLA-4 (Ipilimumab), anti-HuMax-CD20 (Ofatumumab), anti-ABX-Epidermal Growth Factor (Panitumumab), anti-MK-3475 (Pembrolizumab), and conjugates thereof.

Exemplary cytokines include, but are not limited to, erythropoietin, granulocyte colony-stimulating factor (G-CSF), filgrastim, and PEGfilgrastim.

Exemplary hormones include, but are not limited to, human growth hormone, luteinizing hormone (Luveris), and epoetin (Procrit).

Exemplary enzymes include, but are not limited to, alpha-glucosidase (Myozyme), Laronidase (Aldurazyme), IgG-CTLA4 fusion (Orencia), and N-acetylgactosameine 4-Sulfatase (Nagdazyme).

The vectors also optionally contain a polyadenylation signal in operative linkage with the transgene. Generally, a polyadenylation signal will be present downstream, in the transcriptional sense, of the transgene. Polyadenylation signals that are active in eukaryotic cells are known in the art and include, but are not limited to, the SV40 polyadenylation signal, the bovine growth hormone (BGH) polyadenylation signal and the herpes simplex virus thymidine kinase gene polyadenylation signal. The polyadenylation signal directs 3' end cleavage of pre-mRNA, polyadenylation of the pre-mRNA at the cleavage site and termination of transcription downstream of the polyadenylation signal. A core sequence AAUAAA is generally present in the polyadenylation signal. See also Cole et al. (1985) *Mol. Cell. Biol.* 5:2104-2113.

In certain embodiments, vectors that do not contain a transgene can contain a multiple cloning site (MCS), also known as a "polylinker," located between a transcriptional control region (as disclosed above) and a polyadenylation signal, to facilitate insertion of the transgene sequences. In the vectors disclosed herein, the portion comprising transcriptional regulatory sequences (or promoter), a transgene and a polyadenylation signal can be denoted an "expression cassette." A vector can contain one, or more than one, expression cassette.

The vectors optionally contain nucleotide sequences encoding a selection marker that functions in eukaryotic cells, such that when appropriate selection is applied (i.e., when cells are cultured in the presence of a selective agent), cells that do not contain the selection marker die or grow appreciably more slowly that do cells that contain the selection marker. An exemplary selection marker that functions in eukaryotic cells is the glutamine synthetase (GS) gene; selection is applied by culturing cells in medium lacking glutamine or medium containing methionine sulfoximide. Another exemplary selection marker that functions in eukaryotic cells is the gene encoding resistance to neomycin (neo); selection is applied by culturing cells in medium containing neomycin or G418. An exemplary gene encoding neomycin resistance is the TN5 Neo gene. Additional selection markers include sequences encoding dihydrofolate reductase (DHFR, imparts resistance to methotrexate), puromycin-N-acetyl transferase (provides resistance to puromycin) and hygromycin kinase (provides resistance to hygromycin B) hygromycin phosphotransferase, aminoglycoside-3-phosphotransferase, ble, and genes encoding resistance to zeocin. Yet additional selection markers that function in eukaryotic cells are known in the art. Selective agents that can be used in the methods disclosed herein are known in the art and include, but are not limited to, methotrexate, neomycin, geneticin, puromycin, bleomycin, Zeocin, blasticidin, hygromycin, methionine sulfoximine and L-glutamine. The sequences encoding the selection marker described above are operatively linked to a promoter and a polyadenylation signal.

Promoters active in eukaryotic cells are known in the art and include, for example viral promoters (e.g., SV40 early promoter, SV40 late promoter, cytomegalovirus major immediate early (MIE) promoter, herpes simplex virus thymidine kinase (HSV-TK) promoter), EF1-alpha (translation elongation factor-1 α subunit) promoter, Ubc (ubiquitin C) promoter, PGK (phosphoglycerate kinase) promoter, actin promoter and others. See also Boshart et al., GenBank Accession No.K03104; Uetsuki et al. (1989)1 *J. Biol. Chem.* 264:5791-5798; Schorpp et al. (1996) *Nucleic Acids Res.* 24:1787-1788; Hamaguchi et al. (2000)*J. Virology* 74:10778-10784; Dreos et al. (2013) *Nucleic Acids Res.* 41(D1):D157-D164 and the eukaryotic promoter database at http://epd.vital-it.ch, accessed on Jul. 16, 2014. Polyadenylation signals active in eukaryotic cells are known in the art and include, but are not limited to, the SV40 polyadenylation signal, the bovine growth hormone (BGH) polyadenylation signal and the herpes simplex virus thymidine kinase gene polyadenylation signal.

Additional promoters, polyadenylation signals, and transgenes can also be present in the vectors disclosed herein. As stated above, promoters and polyadenylation signals that function in eukaryotic cells are known in the art. Promoters and polyadenylation signals are generally disposed such that nucleotide sequences encoding a polypeptide of interest ("transgene sequences") can be inserted therebetween, in operative linkage with the promoter and polyadenylation signal. In certain embodiments, a multiple cloning site (MCS), also known as a "polylinker," is present between a promoter and a polyadenylation signal, to facilitate insertion of the transgene sequences. In vectors containing transgene sequences, any portion of the vector containing a promoter, transgene sequences and a polyadenylation signal can be denoted the "expression cassette."

In certain embodiments, a vector as disclosed herein can contain two or more expression cassettes; i.e., the vector can express two or more transgenes. For example, a vector containing two expression cassettes, one of which encodes an antibody heavy chain, and the other of which encodes an antibody light chain can be used for production of functional antibody molecules. Expression cassettes can also contain post-transcriptional regulatory elements and/or matrix attachment regions (see below).

In additional embodiments, the vectors disclosed herein can contain two (or more) transgenes in a single expression cassette. In these embodiments, an internal ribosome entry site (IRES) is located between the two transgenes such that a polycistronic transcript (i.e., a transcript containing coding sequence for both transgenes) is produced. Translation of the upstream coding sequences is initiated normally, at the 5' cap of the mRNA, while translation of the downstream coding sequences is initiated at the IRES. IRES sequences are known in the art. Exemplary IRES sequences include picornaviral IRES sequences, such as the encephalomyocarditis virus (EMCV) IRES, the Chenyl IRES and IRES 2A.

The vectors disclosed herein also contain a replication origin that functions in prokaryotic cells. Replication origins that functions in prokaryotic cells are known in the art and include, but are not limited to, the oriC origin of E. coli; plasmid origins such as, for example, the pSC101 origin, the pBR322 origin (rep) and the pUC origin; and viral (i.e., bacteriophage) replication origins. Methods for identifying procaryotic replication origins are provided, for example, in Sernova & Gelfand (2008) Brief Bioinformatics 9(5):376-391.

The vectors disclosed herein can also contain a second selection marker that functions in prokaryotic cells. Selection markers that function in prokaryotic cells are known in the art and include, for example, sequences that encode polypeptides conferring resistance to a selective agent such as, for example, of ampicillin, kanamycin, chloramphenicol, or tetracycline. An example of a polypeptide conferring resistance to ampicillin (and other beta-lactam antibiotics) is the beta-lactamase (bla) enzyme. Kanamycin resistance can result from activity of the neomycin phosphotransferase gene; and chloramphenicol resistance is mediated by chloramphenicol acetyl transferase.

In certain embodiments, the vectors also include, within an expression cassette (as defined above) a post-transcriptional regulatory element (PRE). In certain embodiments, the post-transcriptional regulatory element is a cis-acting element that promotes mRNA stability. In other embodiments, the post-transcriptional regulatory element is a cis-acting element that promotes transport of RNA from the nucleus to the cytoplasm. Exemplary PREs include the human hepatitis B virus PRE (HPRE) and the woodchuck hepatitis virus post-transcriptional regulatory element (WPRE, SEQ ID NO:7). See, e.g., U.S. Pat. No. 6,136,597 (e.g., GenBank Accession No: AR136166); Huang & Liang (1993) Mol. Cell. Biol. 13:7476-7486; Huang & Yen (1994) J. Virol. 68:3193-3199; Donello et al. (1996) J. Virol. 70:4345-4351; and Donello et al. (1998) J. Virology 72:5085-5092. Sub-elements of the HPRE (α element and β element) and WPRE (α element, β element and γ element) have been identified. Accordingly, chimeric PREs containing mixtures of HPRE and WPRE sub-elements are also contemplated for use in the vectors disclosed herein.

Additional post-transcriptional regulatory elements include, but are not limited to, the 5'-untranslated region of the human Hsp70 gene, the SP163 sequence from the vascular endothelial growth factor (VEGF) gene, the tripartite leader sequence associated with adenovirus late mRNAs and the first intron of the human cytomegalovirus immediate early gene. See, for example, Mariati et al. (2010) Protein Expression and Purification 69:9-15.

Accordingly, vectors as disclosed herein can contain a HPRE, a WPRE, hybrids or chimeras thereof, and/or any other type of cis-acting post-transcriptional regulatory element, within the expression cassette portion of the vector, in operative linkage with the transgene sequences, such that a transcript originating from the expression cassette contains sequences encoded by the post-transcriptional regulatory element. As shown in the Examples below, the presence of a PRE in an expression vector can contribute to high-level, stable expression of a transgene encoded by the vector.

In further embodiments, the vectors disclosed herein contain a matrix attachment region (MAR), also known as a scaffold attachment region (SAR). MAR and SAR sequences act, inter alfa, to insulate the chromatin structure of adjacent sequences. Thus, in a stably transformed cell, in which heterologous sequences are often chromosomally integrated, a MAR or SAR sequence can prevent repression of transcription of a transgene that has integrated into a region of the cellular genome having a repressive chromatin structure. Accordingly, inclusion of one or more MAR or SAR sequences in a vector can facilitate expression of a transgene from the vector in stably-transformed cells.

Exemplary MAR and SAR elements include those from the human interferon beta gene (IBM), the chicken (G. gallus) lysozyme gene 5' matrix attachment region (CLM), the human interferon alpha-2 gene (IAM), the mouse S4 MAR/SAR and the human X29 MAR/SAR. The MAR or SAR sequences can be located at any location within the vector. In certain embodiments, MAR and/or SAR elements are located within the expression cassette upstream (in the transcriptional sense) of a promoter.

The vectors disclosed herein can be any nucleic acid vector known in the art. Exemplary vectors include plasmids, cosmids, bacterial artificial chromosomes (BACs) and viral vectors.

Polynucleotides and Oligonucleotides

A polynucleotide is a polymer of nucleotides, and the term is meant to embrace smaller polynucleotides (fragments) generated by fragmentation of larger polynucleotides. The terms polynucleotide and nucleic acid encompass both RNA and DNA, as well as single-stranded and double-stranded polynucleotides and nucleic acids. Polynucleotides also include nucleic acid analogues and modified polynucleotides and nucleic acids, containing such modifications of the base, sugar or phosphate groups as are known in the art.

An oligonucleotide is a short nucleic acid, generally DNA and generally single-stranded. Generally, an oligonucleotide will be shorter than 200 nucleotides, more particularly, shorter than 100 nucleotides, most particularly, 50 nucleotides or shorter.

Modified bases and base analogues, e.g., those able to form Hoogsteen and reverse Hoogsteen base pairs with the naturally-occurring bases, are known in the art. Examples include, but are not limited to, 8-oxo-adenosine, pseudoisocytidine, 5-methyl cytidine, inosine, 2-aminopurine and various pyrrolo- and pyrazolopyrimidine derivatives. Similarly, modified sugar residues or analogues, for example 2'-O-methylribose or peptide nucleic acid backbones, can also form a component of a modified base or base analogue. See, for example, Sun and Helene (1993) *Curr. Opin. Struct. Biol.* 3:345-356. New modified bases, base analogues, modified sugars, sugar analogues, modified phosphates and phosphate analogues capable of participating in duplex or triplex formation are available in the art, and are useful in the methods and compositions disclosed herein.

Polynucleotides of any length, comprising one or more of the sequences disclosed herein, are provided. Such polynucleotides are 10 or more, 12 or more, 14 or more, 15 or more, 16 or more, 18 or more, 20 or more, 25 or more, 50 or more, 75 or more, 100 or more, 200 or more, 500 or more, or 1,000 or more nucleotides in length. Nucleic acids having a sequence that is 50%, 55%, 60%, 65%, 70%, 75%, 80%, 85%, 90%, 95%, 96%, 97%, 98%, 99% or 99.9% identical to the sequences disclosed herein are also provided. Nucleic acids comprising nucleotide sequences that are complementary to the sequences disclosed herein are also provided, as are nucleic acids that hybridize to the aforementioned nucleic acids under stringent conditions.

The subject nucleic acids can optionally comprise heterologous nucleotide sequences. Such heterologous nucleotide sequences can be regulatory sequences, such as promoters, operators, enhancers, terminators and the like; or can encode heterologous amino acid (i.e., polypeptide) sequences.

Homology and Identity of Nucleic Acids

"Homology" or "identity" or "similarity" as used herein refers to the relationship between two nucleic acid molecules based on an alignment of their nucleic acid sequences. Homology and identity can each be determined by comparing a position in each sequence which may be aligned for purposes of comparison. For example, a "reference sequence" can be compared with a "test sequence." When a position in the reference sequence is occupied by the same nucleotide at an equivalent position in the test sequence, then the molecules are identical at that position; when the equivalent position is occupied by a similar nucleotide residue (e.g., similar in steric and/or electronic nature, and/or in its hydrogen-bonding properties), then the molecules can be referred to as homologous (similar) at that position. The relatedness of two sequences, when expressed as a percentage of homology/similarity or identity, is a function of the number of identical or similar nucleotides at positions shared by the sequences being compared. In comparing two sequences, the absence of nucleotide residues, or presence of extra residues, in one sequence as compared to the other, also decreases the identity and homology/similarity.

As used herein, the term "identity" refers to the percentage of identical nucleotide residues at corresponding positions in two or more sequences when the sequences are aligned to maximize sequence matching, i.e., taking into account gaps and insertions. Identity can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the highest degree of match between the sequences tested. Moreover, methods to determine identity are codified in publicly available computer programs. Computer program methods to determine identity between two sequences include, but are not limited to, the GCG program package (Devereux et al. (1984) *Nucleic Acids Research* 12:387), BLASTP, BLASTN, and FASTA (Altschul et al. (1990) *J. Molec. Biol.* 215:403-410; Altschul et al. (1997) *Nucleic Acids Res.* 25:3389-3402). The BLAST X program is publicly available from NCBI and other sources. See, e.g., BLAST Manual, Altschul, S., et al., NCBI NLM NIH Bethesda, Md. 20894; Altschul et al. (1990) *J. Mol. Biol.* 215:403-410. The well known Smith-Waterman algorithm can also be used to determine identity.

For sequence comparison, typically one sequence acts as a reference sequence, to which one or more test sequences are compared. Sequences are generally aligned for maximum correspondence over a designated region, e.g., a region at least about 15, 20, 25, 30, 35, 40, 45, 50, 55, 60, 65 or more nucleotides in length, and the region can be as long as the full-length of the reference nucleotide sequence. When using a sequence comparison algorithm, test and reference sequences are input into a computer program, subsequence coordinates are designated, if necessary, and sequence algorithm program parameters are designated. The sequence comparison algorithm then calculates the percent sequence identity for the test sequence(s) relative to the reference sequence, based on the designated program parameters.

Examples of algorithms that are suitable for determining percent sequence identity are the BLAST and BLAST 2.0 algorithms, which are described in Altschul et al. (1990) *J. Mol. Biol.* 215:403-410 and Altschul et al. (1977) *Nucleic Acids Res.* 25:3389-3402, respectively. Software for performing BLAST analyses is publicly available through the National Center for Biotechnology Information at www.ncbi.nlm.nih.gov (visited Dec. 27, 2012). Further exemplary algorithms include ClustalW (Higgins et al. (1994) *Nucleic Acids Res.* 22:4673-4680), available at www.ebi.ac.uk/Tools/clustalw/index.html (visited Dec. 27, 2012).

Sequence identity between two nucleic acids can also be described in terms of annealing, reassociation, or hybridization of two polynucleotides to each other, mediated by base-pairing. Hybridization between polynucleotides proceeds according to well-known and art-recognized base-pairing properties, such that adenine base-pairs with thymine or uracil, and guanine base-pairs with cytosine. The property of a nucleotide that allows it to base-pair with a second nucleotide is called complementarity. Thus, adenine is complementary to both thymine and uracil, and vice versa; similarly, guanine is complementary to cytosine and vice versa. An oligonucleotide or polynucleotide which is complementary along its entire length with a target sequence is said to be perfectly complementary, perfectly matched, or fully complementary to the target sequence, and vice versa. Two polynucleotides can have related sequences, wherein the majority of bases in the two sequences are complementary, but one or more bases are noncomplementary, or mismatched. In such a case, the sequences can be said to be substantially complementary to one another. If two polynucleotide sequences are such that they are complementary at all nucleotide positions except one, the sequences have a single nucleotide mismatch with respect to each other.

Conditions for hybridization are well-known to those of skill in the art and can be varied within relatively wide limits. Hybridization stringency refers to the degree to which hybridization conditions disfavor the formation of hybrids containing mismatched nucleotides, thereby promoting the formation of perfectly matched hybrids or hybrids containing fewer mismatches; with higher stringency correlated with a lower tolerance for mismatched hybrids. Factors that affect the stringency of hybridization include, but are not limited to, temperature, pH, ionic strength, and concentration of organic solvents such as formamide and dimethylsulfoxide. As is well known to those of skill in the art, hybridization stringency is increased by higher temperatures, lower ionic strengths, and lower solvent concentrations. See, for example, Ausub el et al., supra; Sambrook et al., supra; M. A. Innis et al. (eds.) PCR Protocols, Academic Press, San Diego, 1990; B. D. Hames et al. (eds.) Nucleic Acid Hybridisation: A Practical Approach, IRL Press, Oxford, 1985; and van Ness et al., (1991) *Nucleic Acids Res.* 19:5143-5151.

Thus, in the formation of hybrids (duplexes) between two polynucleotides, the polynucleotides are incubated together in solution under conditions of temperature, ionic strength, pH, etc., that are favorable to hybridization, i.e., under hybridization conditions. Hybridization conditions are chosen, in some circumstances, to favor hybridization between two nucleic acids having perfectly-matched sequences, as compared to a pair of nucleic acids having one or more mismatches in the hybridizing sequence. In other circumstances, hybridization conditions are chosen to allow hybridization between mismatched sequences, favoring hybridization between nucleic acids having fewer mismatches.

The degree of hybridization between two polynucleotides, also known as hybridization strength, is determined by methods that are well-known in the art. A preferred method is to determine the melting temperature ($T_m$) of the hybrid duplex. This is accomplished, for example, by subjecting a duplex in solution to gradually increasing temperature and monitoring the denaturation of the duplex, for example, by absorbance of ultraviolet light, which increases with the unstacking of base pairs that accompanies denaturation. $T_m$ is generally defined as the temperature midpoint of the transition in ultraviolet absorbance that accompanies denaturation. Alternatively, if $T_m$s are known, a hybridization temperature (at fixed ionic strength, pH and solvent concentration) can be chosen that is below the $T_m$ of the desired duplex and above the $T_m$ of an undesired duplex. In this case, determination of the degree of hybridization is accomplished simply by testing for the presence of duplex polynucleotide. Adsorption to hydroxyapatite can also be used to distinguish single-stranded nucleic acids from double-stranded nucleic acids.

Hybridization conditions are selected following standard methods in the art. See, for example, Sambrook, et al., Molecular Cloning: A Laboratory Manual, Second Edition, (1989) Cold Spring Harbor, N.Y. For example, hybridization reactions can be conducted under stringent conditions. An example of stringent hybridization conditions is hybridization at 50° C. or higher in 0.1× SSC (15 mM sodium chloride/1.5 mM sodium citrate). Another example of stringent hybridization conditions is overnight incubation at 42° C. in a solution: 50% formamide, 5× SSC (0.75 M NaCl, 75 mM trisodium citrate), 50 mM sodium phosphate (pH7.6), followed by washing in 0.1× SSC at about 65° C. Optionally, one or more of 5× Denhardt's solution, 10% dextran sulfate, and/or 20 mg/ml heterologous nucleic acid (e.g., yeast tRNA, denatured, sheared salmon sperm DNA) can be included in a hybridization reaction. Stringent hybridization conditions are hybridization conditions that are at least as stringent as the above representative conditions, where conditions are considered to be at least as stringent if they are at least about 80% as stringent, typically at least 90% as stringent as the above specific stringent conditions.

The term "substantially identical" is used herein to refer to a first nucleic acid sequence that contains a sufficient or minimum number of nucleotides that are identical to aligned nucleotides in a second nucleic acid sequence such that the first and second nucleotide sequences possess a common functional property (e.g., enhancing the expression, stability or transport of mRNA).

The term "homology" describes a mathematically based comparison of sequence similarities which is used to identify sequences with similar functions or motifs. A reference nucleotide sequence (e.g., a sequence as disclosed herein) is used as a "query sequence" to perform a search against public databases to, for example, identify other family members, related sequences or homologues. Such searches can be performed using the NBLAST and)(BLAST programs (version 2.0) of Altschul et al. (1990) *J. Mol. Biol.* 215:403-410. BLAST nucleotide searches can be performed with the NBLAST program, score=100, wordlength=12 to obtain nucleotide sequences homologous to a reference nucleotide sequence. To obtain gapped alignments for comparison purposes, Gapped BLAST can be utilized as described in Altschul et al. (1997) *Nucleic Acids Res.* 25:3389-3402. When utilizing the BLAST and Gapped BLAST programs, the default parameters of the respective programs (e.g.,)(BLAST and BLAST) can be used (see the world wide web at: ncbi.nlm.nih.gov).

Nucleic acids and polynucleotides of the present disclosure encompass those having an nucleotide sequence that is at least 50%, at least 60%, at least 70%, at least 75%, at least 80%, at least 85%, at least 90%, at least 95%, at least 98%, at least 99%, at least 99.9% or 100% identical to any of SEQ ID NOs:1-6.

Nucleotide analogues are known in the art. Accordingly, nucleic acids (i.e., SEQ ID NOs:1-6) comprising nucleotide analogues are also encompassed by the present disclosure.

Cells and cell culture

The present disclosure provides methods for expressing a recombinant polypeptide in a cell. The methods comprise introducing a vector as described herein into a cell and culturing the cell under conditions in which the vector is either transiently or stably maintained in the cell. Cells can be procaryotic or eukaryotic. Cultured eukaryotic cells, that can be used for expression of recombinant polypeptides, are known in the art. Such cells include fungal (e.g., yeast) cells, insect cells, plant cells and mammalian cells. Accordingly, the disclosure provides a cell comprising a vector as described herein.

Exemplary prokaryotic cells include *E. coli, B. subtilis* and *S. typhimurium.*

Exemplary yeast cells include, but are not limited to, *Trichoderma* sp., *Pichia pastoris, Schizosaccharomyces pombae* and *Saccharomyces cerevisiae.* Exemplary insect cell lines include, but are not limited to, Sf9, Sf21, and Drosophila S2 cells. Exemplary plant cells include, but are not limited to, Arabidopsis cells and tobacco BY2 cells.

Cultured mammalian cell lines, useful for expression of recombinant polypeptides, include Chinese hamster ovary (CHO) cells, human embryonic kidney (HEK) cells, virally transformed HEK cells (e.g., HEK293 cells), NS0 cells, SP20 cells, CV-1 cells, baby hamster kidney (BHK) cells, 3T3 cells, Jurkat cells, HeLa cells, COS cells, PERC.6 cells, CAP® cells and CAP-T® cells (the latter two cell lines being commercially available from Cevec Pharmaceuticals, Cologne, Germany). A number of derivatives of CHO cells are also available such as, for example, CHO-DXB11, CHO-DG-44, CHO-K1 and CHO-S. Derivatives of any of the cells described herein obtained, for example, by mutagenesis, selection, gene knock-out, targeted integration (e.g., CRISPR/CAS9; zinc finger nucleases) or cloning, are also provided. Mammalian primary cells can also be used. Myeloma and hybridoma cells can also be used.

In certain embodiments, the cells are cultured in a medium containing serum. In additional embodiments, the cells are cultured in serum-free medium. For example, for manufacture of therapeutic proteins for administration to patients, expressing cells must be grown in serum-free medium. In additional embodiments, the cells have been pre-adapted for growth in serum-free medium prior to being used for polypeptide expression.

The vectors as described herein can be introduced into any of the aforementioned cells using methods that are known in the art. Such methods include, but are not limited to, polyethylene glycol (PEG)-mediated methods, electroporation, biolistic delivery (i.e., particle bombardment), protoplast fusion, DEAE-dextran-mediated methods, calcium phosphate co-precipitation, lipid-based particles (e.g., lipofection) and targeted integration (e.g., CRISPR/CAS9; zinc finger nucleases). See also, Sambrook et al. "Molecular Cloning: A Laboratory Manual," Third Edition, Cold Spring Harbor Laboratory Press, 2001; and Ausubel et al., "Current Protocols in Molecular Biology," John Wiley & Sons, New York, 1987 and periodic updates.

Standard methods for cell culture are known in the art. See, for example, R. I. Freshney "Culture of Animal Cells: A Manual of Basic Technique," Fifth Edition, Wiley, New York, 2005.

Long-term, stable expression of recombinant polypeptides

The inventors have made the surprising discovery that, with respect to expression of recombinant polypeptides, inclusion of a post-transcriptional regulatory element sequence (PRE) in operative linkage with sequences encoding the polypeptide, in a vector, leads to both (1) a higher frequency of cells expressing the polypeptide following introduction of the vector into a population of cells, and (2) much more stable and longer-term expression of the recombinant polypeptide than has been achieved with other expression systems. See Example 5 below.

Accordingly, the present disclosure provides methods for expressing a polypeptide in a population of cells by contacting (e.g., transfecting) the cells with a vector containing a PRE in operative linkage with a transgene encoding the polypeptide. The vector can also contain any of the elements disclosed herein; e.g., CMV transcriptional regulatory sequences, any of SEQ ID NOs:1-6, sequences substantially identical to any of SEQ ID NOs:1-6, promoters, enhancers, polyadenylation signals, MAR/SAR elements, selection markers, replication origins, etc. In certain embodiments, over 10%, over 20%, over 25%, over 30%, over 40%, over 50%, over 60%, over 70%, or over 80% of the cells in the population express the polypeptide encoded by the transgene.

In additional embodiments, after contacting (e.g., transfecting) cells with a vector containing a PRE in operative linkage with a transgene encoding a polypeptide, the cells express the polypeptide for 5 or more, 10 or more, 20 or more, 25 or more, 30 or more, 35 or more, 40 or more, 45 or more, or 50 or more generations. The vector can also contain any of the elements disclosed herein; e.g., CMV transcriptional regulatory sequences, any of SEQ ID NOs:1-6, sequences substantially identical to any of SEQ ID NOs:1-6, promoters, enhancers, polyadenylation signals, MAR/SAR elements, selection markers, replication origins, etc.

EXAMPLES

Example 1: Construction of a Human Growth Hormone Expression Vector

Figure 1:
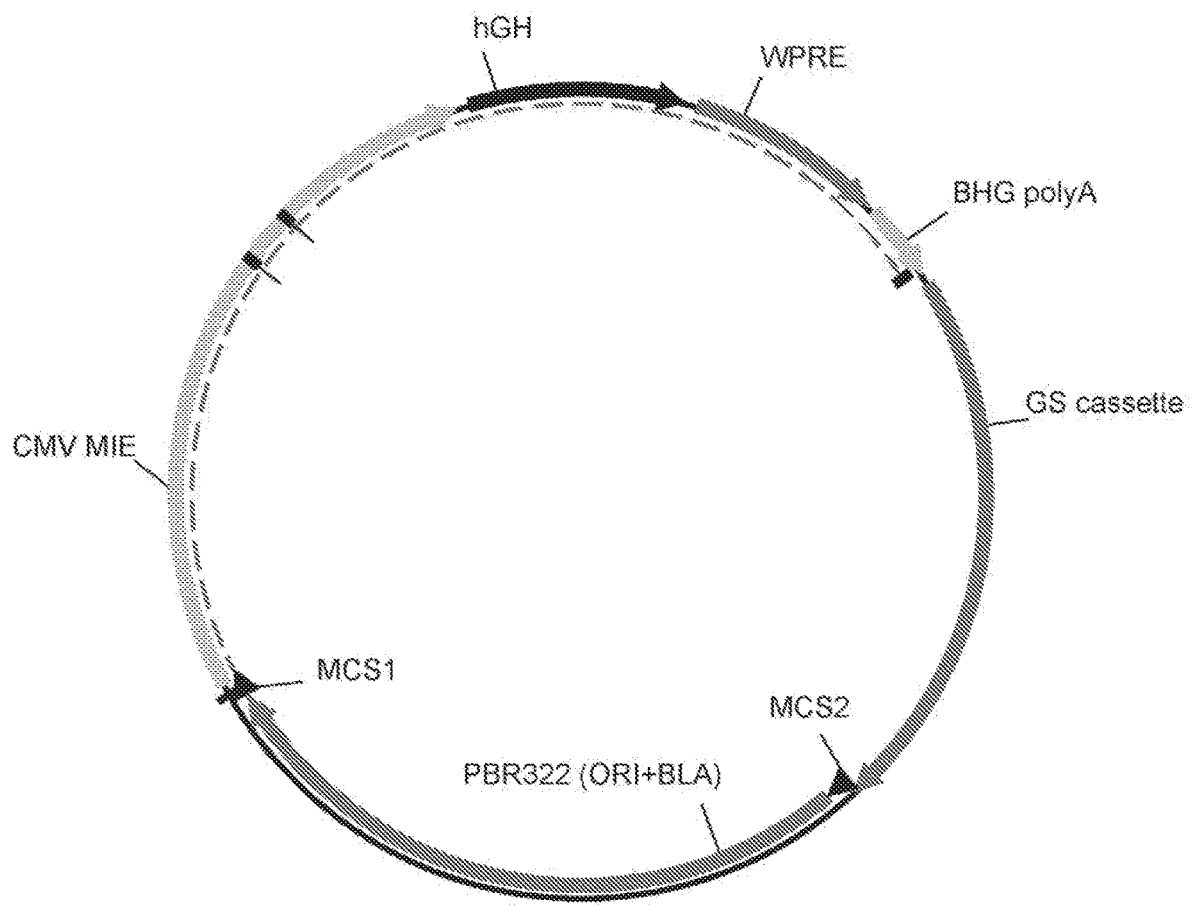
FIG. 1 is a schematic diagram showing an exemplary expression vector containing a glutamine synthetase (GS) selection cassette; an expression cassette that includes the CMV MIE promoter, transgene sequences encoding human growth hormone (hGH), a WPRE, and the BGH polyadenylation signal (BHG polyA); two multiple cloning sites (MCS1 and MCS2); the pBR322 replication origin (ori) and the pBR322 beta-lactamase (bla) gene.

A selection cassette containing a SV40 early promoter, sequences encoding glutamine synthetase (GS) and a SV40 polyadenylation signal, flanked by multiple cloning sites (MCS), was constructed by gene synthesis and inserted into the pUC57 vector. Separately, a hGH expression cassette containing a CMV MIE promoter, sequences encoding human growth hormone, a WPRE, and a bovine growth hormone polyadenylation signal was constructed in pUC57. The selection cassette, including the flanking MCS, was removed from the pUC57 backbone and inserted between the NdeI and EcoRI sites of pBR322 to generate a GS vector. Finally, the hGH expression cassette was removed from the pUC57 backbone and inserted into the GS vector. The resulting plasmid contains ori and bla sequences from pBR322, a GS selection cassette, and a hGH expression cassette. A schematic diagram of the vector is shown in FIG. 1.

Example 2: Expression of Human Growth Hormone in CHO-K1 Cells

CHO-K1 cells were cultured in Dulbecco's Modified Eagle's Medium (DMEM, Corning) supplemented with 1% L-proline (17.3 g/L) and 10% fetal bovine serum (FBS). After five passages, viability was 95.3%, with a viable cell density (VCD) of $0.88 \times 10^6$ cells/ml. At that time, $4 \times 10^5$ cells were seeded in a 35 mm dish (in a 6-well plate) in 2.5 ml of DMEM +1% L-proline (17.3 g/L) and 10% FBS. The following day, medium was replaced with fresh medium and the cells were transfected with the vector described in Example 1 and FIG. 1.

For transfection, 4 µg of DNA in 0.25 ml of OptiMEM was mixed with 12.5 µl Lipofectamine 2000 in 0.25 ml OptiMEM. The mixture was applied to the cells and incubated for 25 min at room temperature.

After 72 hours, conditioned medium was collected from the cultures and tested for hGH levels by protein blotting.

Blots were probed with a mouse monoclonal antibody to human growth hormone (Thermo Scientific, Catalogue No. MS-1328-P0) used at a 1:800 dilution. Blots were then exposed to a peroxidase-conjugated goat anti-mouse secondary antibody (Jackson Laboratories, Catalogue No. 115-035-166), used at a 1:20,000 dilution. Blots were then exposed to peroxidase substrate (Western Blot Reagent ECL 2, Thermo Scientific), then dried and exposed for 3 min in a Kodak 1000 imaging system.

Figure 2:
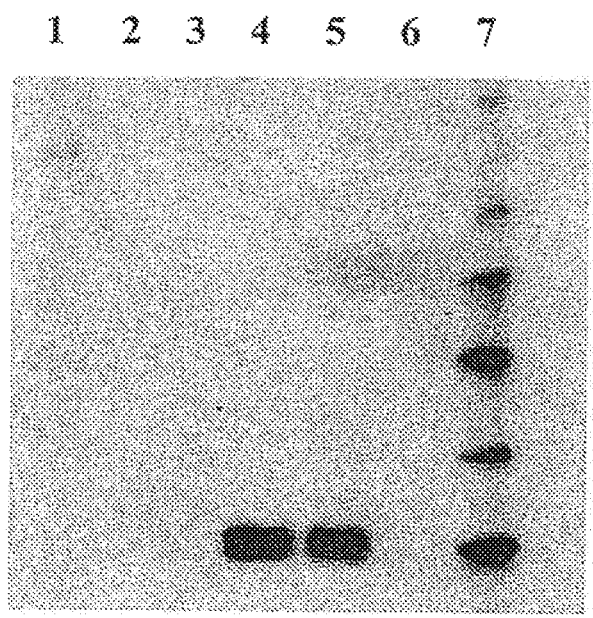
FIG. 2 shows the results of a protein blotting assay for human growth hormone expression in CHO-K1 cells transfected with the expression vector shown in FIG. 1. Lane 1: markers; Lane 2: hGH standard, 15 pg; Lane 3: hGH standard, 90 pg; Lane 4: CHO-K1 cells transfected with 4 ug of expression vector DNA; Lane 5: CHO-K1 cells transfected with 6 ug of expression vector DNA; Lane 6: untransfected CHO-K1 cells; Lane 7: markers (the three lowest bands represent 20, 30 and 40 KDa, in ascending order).
Figure 3:
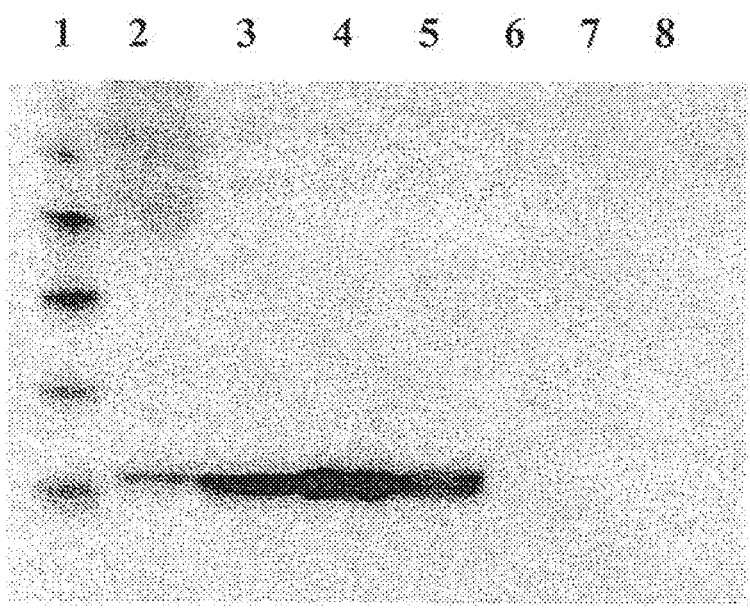
FIG. 3 shows the results of a protein blotting assay for human growth hormone expression in suspension/serum-free adapted CHO-K1 cells (SSA-CHO-K1) and control cells electroporated with the expression vector shown in FIG. 1. Lane 1: markers (the three lowest bands representing 20, 30 and 40 KDa, in ascending order); Lane 2: sample shown in Lane 4 of FIG. 2; Lane 3: electroporated SSA-CHO-K1 cells, recovery medium #1; Lane 4: positive control cells (CHO-S, Life Technologies); Lane 5: electroporated SSA-CHO-K1 cells, recovery medium #2; Lane 6: untransfected SSA-CHO-K1 cells, recovery medium #1; Lane 7:untransfected CHO-S control cells; Lane 8: untransfected SSA-CHO-K1 cells, recovery medium #2.

Representative results are shown in FIG. 2. As can be seen in Lanes 4 and 5, overexpression of hGH is observed in the transfected CHO-K1 cells.

Example 3: Expression of Human Growth Hormone in CHO-K1 Cell Derivatives

CHO-K1 cells were adapted for growth in suspension and for growth in serum-free medium. These suspension/serum-free growth-adapted cells (SSA-CHO-K1) were cultured in CDOptiCHO medium (Life Technologies, Carlsbad, CA) supplemented with Glutamax 100× (Life Technologies). The cells were transfected with the vector described in Example 1 and FIG. 1. For transfection, 1×10$^7$ cells were pelleted by centrifugation, and resuspended in 0.5 ml of transfection medium (CDCHO, Life Technologies). Cells were transfected by electroporation, using a Gene Pulsar II device (BioRad, Hercules, Calif.). Electroporation was conducted using 20 µg DNA at a voltage of 300V and a capacitance of 900 µF for 18-21 msec in a 0.4 cm cuvette.

Electroporated cells were transferred into 2 ml of recovery medium in a 6-well plate. Two different recovery media were tested. Cells were harvested at 72 hours after electroporation and analyzed for hGH expression by protein blotting. Conditions for protein blotting and analysis were the same as those described in Example 2, except that the blots were exposed for one minute in the imaging system.

Figure 4:
FIG. 4 is a schematic diagram showing an exemplary expression vector containing a glutamine synthetase (GS) selection cassette; an expression cassette that includes the CMV MIE promoter, transgene sequences encoding human growth hormone (hGH), and the BGH polyadenylation signal (BHG polyA); two multiple cloning sites (MCS1 and MCS2); the pBR322 replication origin (ori) and the pBR322 beta-lactamase (bla) gene.

The results, shown in FIG. 4, indicate that the hGH expression vector functions in CHO-derived cell lines such as SSA-CHO-K1 and CHO-S. hGH expression in serum-free/suspension adapted CHO-K1 cells transfected by electroporation (lanes 3 and 5) is approximately 5-fold greater than in CHO-K1 cells transfected with Lipofectamine (which expressed hGH at a level of 2.5 µg/ml), as was described in Example 2 (Lane 2).

Example 4: Effect of a Post-transcriptional Regulatory Element on hGH Expression A derivative of the expression vector described in Example 1 was constructed in which the WPRE was removed, and the WPRE-containing vector (W-vector) was compared with the vector lacking a WPRE (O-vector) with respect to hGH expression in transfected cells. The cell lines used were two lots of the SSA-CHO-K1 cells used in the previous example and a control cell line, CHO-S (Life Technologies). Cell culture and electroporation were the same as described in Example 3. Protein blotting analysis and imaging time were the same as described in Example 3.

Figure 5:
FIG. 5 shows the results of a protein blotting assay for human growth hormone expression in two different preparations of suspension/serum-free adapted CHO-K1 (SSA-CHO-K1) cells (Prep A and Prep B) and control cells (CHO-S, Life Technologies). A vector containing a WPRE (W-vector) operatively linked to hGH sequences was compared with a vector that did not contain a WPRE (O-vector). pcDNA 3.1 hGH was used a s a positive control vector.
Lane 1: Prep A cells, W-vector
Lane 2: Prep A cells, O-vector
Lane 3: Prep B cells, W-vector
Lane 4: Prep B cells, O-vector
Lane 5: Prep A cells, untransfected
Lane 6: Prep B cells, untransfected
Lane 7: CHO-S cells, W-vector
Lane 8: CHO-S cells, O-vector
Lane 9: CHO-S cells, untransfected
Lane 10: CHO-S cells, pcDNA 3.1 hGH
Lane 11: Prep A cells, pcDNA 3.1 hGH
Lane 12: Prep B cells, pcDNA 3.1 hGH

The results, shown in FIG. 5, indicate that the presence of a WPRE, in operative linkage with the hGH transgene sequences in the expression vector, stimulates expression of hGH by CHO-K1 cells.

Example 5: Effect of 5' Untranslated Region on Expression of Linked Coding Sequences The CMV-derived transcriptional regulatory sequences disclosed herein comprise a RC-dUTR, promoter/enhancer sequences, a uUTR, an intron, and a dUTR. To assess the contributions of these different elements to transcription, a series of vector constructs containing a Rituximab (Rtx) light-chain-expressing transgene was constructed. An undeleted constructs containing all of the elements was designated pCT 2.1. In one vector (pCT 2.36), only the intron was deleted; in another (pCT 2.39) the uUTR, intron and dUTR were deleted, and, in fourth construct (pCT 2.51), the RC-dUTR, uUTR, intron and dUTR were deleted. See FIG. 6.

The vectors described above were introduced into CHO cells by electroporation as described in Example 3. After 48 hours, conditioned medium from transfected cells was harvested for determination of Rtx level by ELISA (see Example 6 for procedure). Absorbance values from the ELISA assays were converted to Rtx titer, using a Rtx standard curve.

FIG. 7 shows that, in vectors lacking a PRE, removal of the intron (pCT 2.36) had no effect on Rtx levels, compared to a vector (pCT 2.1) in which none of the transcriptional control elements were deleted. However, if, in addition to the intron, the upstream and downstream portions of the 5' untranslated region were also deleted (pCT 2.39), lower levels of Rtx were produced. Finally, if the RC-dUTR sequence was also deleted, leaving only the promoter/enhancer sequences present (pCT 2.51), Rtx levels were reduced to less than half of those observed when all elements were present.

These data indicate that the 5' untranslated sequences of the CMV MIE transcriptional regulatory region contribute strongly to the expression of linked coding sequences, with the RC-dUTR sequence having a particularly powerful effect.

Example 6: Effect of PRE on Number of Stable, High-expressing Clones

Plasmids expressing the light chain and heavy chain of the anti-CD20 antibody Rituximab were used to test the effect of a PRE on expression levels and stability of expression. In one set of experiments, cells were transfected with a pair of plasmids, both containing PRE sequences, and one of which contained light-chain-encoding sequences (LC+PRE) and one of which contained heavy-chain-encoding sequences (HC+PRE). In parallel experiments, cells were transfected with a pair of plasmids, both lacking PRE sequences, and one of which contained light-chain-encoding sequences (LC−PRE) and one of which contained heavy-chain-encoding sequences (HC−PRE). Schematic diagrams of these vectors are shown in FIG. 8.

For electroporation, CHO cells, adapted for growth in serum-free medium, were grown in suspension culture in serum-free medium. LC and HC vectors were introduced into cells by electroporation as described in Example 3. Forty-eight hours after electroporation, cells were transferred into flasks containing serum-free medium and incubated at 37° C.

Following recovery, stable pools were selected in serum-free medium containing 20-60 µM Methionine Sulfoximine (MSX, Sigma-Aldrich Chemical Co., St. Louis, Mo.) for approximately 2-3 weeks. After 2-3 weeks of selection cell viability dropped to 20% and stable pools appeared with viability reaching >97%.

To generate stable mini-pools, 50-100 cells/well were plated in medium containing 25 µM MSX in 96-well plates. To obtain single clones, 0.1-0.5cell/well were plated in 96 well plates by limiting dilution in medium containing 25-50 uM MSX. After 2-3 weeks, the pools, mini-pools and clones were screened for expression of complete Rtx antibody (heavy and light chains) by ELISA, and for stability.

For ELISA, plates were coated with goat anti-human IgG Fab (Jackson Immuno Research, West Grove, Pa.) polyclonal antibody and detected with Horseradish peroxidase (HRP)-conjugated Goat anti human Fc. OPD (o-phenylenediamine) was used as a substrate for HRP and absorption was measured at 480 nM using a Polar Star microplate reader (BMG Labtech, Inc., Cary, N.C.). Viable cell density (VCD) and viability were measured using a ViCell® Analyzer (Beckman Coulter, Brea, Calif.).

To assess stability, stable pools, mini-pools and clones were further passaged for 25-50 generations in serum-free medium containing MSX. At various passages, new cultures were set up in shake flasks in batch mode for 8-11 days in shaker flasks. When cell culture viability dropped to ~70-75% cultures were harvested and samples were assayed for Rtx expression by ELISA.

An analysis of Rtx expression in mini-pools obtained from cells transfected with a PRE-containing vector is shown in FIG. 9; and a similar analysis of Rtx expression in mini-pools obtained from cells transfected with a vector that did not contain a PRE is shown in FIG. 10. Quantitative data are shown in Tables 1 and 2 for PRE-containing and PRE-lacking vectors, respectively. As can be seen from these data, over half of the mini-pools obtained from cells transfected with the PRE-containing vector were positive for Rtx expression; while only 10-20% of mini-pools obtained from cells transfected with a PRE-lacking vector were positive for Rtx expression.

TABLE 1

Rtx expression in cells transfected with a PRE-containing vector

| Category | OD Range | 9×96 well plates | Total colonies | Percent of total wells screened | Percent positive |
|---|---|---|---|---|---|
| Total wells screened | 0.0-2.2 | 586 | 236 | | 50-60% |
| High | >2 | 11 | | | |
| | 1.5-2 | 18 | 29 | 12% | |
| Med | 1-1.5 | 24 | | | |
| | 0.5-1 | 36 | 60 | 25% | |
| Low | 0.4-0.5 | 44 | 44 | 18.6% | |
| Ultra low | 0.3-0.4 | 86 | 86 | 36% | |
| Blank | 0.2-0.3 | 350 | 350 | | |
| | .0-0.2 | 279 | no colonies | | |

TABLE 2

Rtx expression in cells transfected with a vector lacking a PRE

| Category | OD Range | 9×96 well plates | Total colonies | Percent of total wells screened | Percent positive |
|---|---|---|---|---|---|
| Total wells screened | 0.0-2.2 | 586 | 250 | | 10-20% |
| High | >2 | 1 | | 0.17% | |
| | 1.5-2 | 29 | 30 | 12% | |
| Med | 1-1.5 | 44 | 44 | 17.6% | |
| Low | 0.5-1 | 450 | 176 | 70% | |
| Blank | 0.4-0.5 | | | | Blank |
| | 0.3-0.4 | | | | |
| | 0.2-0.3 | | | | |
| | 0-0.2 | | | | |

Analysis of a representative mini-pool obtained from cells transfected with PRE-containing LC- and HC-expressing vectors is shown in FIG. 11. This mini-pool expresses almost 800-fold higher levels of Rtx than a pool obtained from cells transfected with LC- and HC-expressing vectors lacking PREs, when cultured under fed batch conditions.

Single clones were also analyzed for Rtx expression, as shown in FIGS. 12 and 13, and provided similar results. From ten 96-well plates seeded at limiting dilution with cells that had been transfected with PRE-containing vectors, 117 clones were obtained. Using a value of 0.2 absorbance units in the ELISA assay as the threshold for expression of Rtx, 50 of the 117 clones (42.7%) were found to be positive for Rtx expression and, of those, 33 clones (28.2%) yielded absorbance values >0.5 (FIG. 12). When cultured under fed batch conditions, individual clones typically expressed greater than 1 gram of recombinant protein per liter of culture.

By contrast, out of 74 clones obtained from 960 wells seeded at limiting dilution with cells that had been transfected with vectors lacking a PRE, only 12 clones (16.2%) were positive for Rtx expression, and only 9 of those (12.1%) yielded absorbance values >0.5 (FIG. 13).

Stability of expression was determined by passaging mini-pools or single clones for up to 50 generations after selection. Batch cultures were set up at various passages by inoculating shake flasks with $0.3 \times 10^6$ cells/ml at >97% viability in 30ml medium, and culturing the samples for 7-10 days in batch mode with no additional feeding or supplements. Viable cell density (VCD) and viability were monitored, and cells were harvested when the viability of the culture dropped below 70-75%, and assayed for Rtx levels by ELISA.

FIG. 14 shows that, for stable pools from cells transfected with expression plasmids containing a PRE, high expression levels (i.e., >30 mg/L) were obtained at passages 7, 11, 17 and 30 in batch culture. By contrast, for cells transfected with vectors lacking a PRE, low levels of Rtx expression (<1.5 mg/L) were obtained at passage 7, and no expression was detectable by passage 11 (FIG. 15).

High-level expression of Rtx was also observed with single clones derived from cells that had been transfected with Rtx-expressing plasmids containing a PRE. FIG. 16 shows data for two such clones grown in batch culure, in which titers of between 90-200 mg/L Rtx were obtained for as long as 51 passages.

The foregoing results indicate that the presence of a PRE in an expression vector increases the number of high-expressing cells descended from cells transfected with such a vector, and that such high-expressing cells are remarkably stable; i.e., they continue to express high levels of protein for at least 50 generations.

All patents, publications and patent applications mentioned herein are hereby incorporated by reference, in their entireties, for all purposes.

What is claimed is:

1. A polynucleotide comprising a cytomegalovirus (CMV) major immediate early (MIE) promoter consisting of the nucleotide sequence of SEQ ID NO:3, a transgene, a polyadenylation signal, and a woodchuck hepatitis virus post transcriptional regulatory element (WPRE) consisting of the nucleotide sequence of SEQ ID NO:7.

2. The polynucleotide of claim 1, further comprising a multiple cloning site.

3. The polynucleotide of claim 1, further comprising a matrix attachment region and/or scaffold attachment region (MAR/SAR) sequence.

4. The polynucieotide of claim 1, wherein the MAR/SAP sequence is selected from the group consisting of a chicken lysozyme MAR/SAR (CLM) sequence, an interferon alpha-2 MAR/SAR (IAM) sequence, an interferon beta MAR/SAR (IBM) sequence, a X29 MAR/SAR sequence, a S4 MAR/SAR sequence and hybrids thereof.

5. The polynucleotide of claim 1, wherein the transgene is a gene that encodes a protein selected from the group consisting a recombinant protein, a fusion protein, an antibody, a cytokine, a hormone, an enzyme and a clotting factor.

6. A cell comprising the polynucleotide of claim 1, wherein the cell is selected from the group consisting of a prokaryotic cell and a eukaryotic cell.

* * * * *

SEQUENCE LISTING

<160> NUMBER OF SEQ ID NOS: 7

<210> SEQ ID NO 1

<211> LENGTH: 2125
<212> TYPE: DNA
<213> ORGANISM: Artificial Sequence
<220> FEATURE:
<223> OTHER INFORMATION: Synthetic

<400> SEQUENCE: 1

| | | | | | |
|---|---|---|---|---|---|
| gtgtcaagga | cggtgactgc | agtgaataat | aaaatgtgtg | tttgtccgaa | atacgcgttt | 60 |
| tgagatttct | gtcgccgact | aaattcatgt | cgcgcgatag | tggtgtttat | cgccgataga | 120 |
| gatggcgata | ttggaaaaat | cgatatttga | aaatatggca | tattgaaaat | gtcgccgatg | 180 |
| tgagtttctg | tgtaactgat | atcgccattt | ttccaaaagt | gattttttggg | catacgcgat | 240 |
| atctggcgat | agcggcttat | atcgtttacg | ggggatggcg | atagacgact | ttggtgactt | 300 |
| gggcgattct | gtgtgtcgca | aatatcgcag | tttcgatata | ggtgacagac | gatatgaggc | 360 |
| tatatcgccg | atagaggcga | catcaagctg | gcacatggcc | aatgcatatc | gatctataca | 420 |
| ttgaatcaat | attggccatt | agccatatta | ttcattggtt | atatagcata | aatcaatatt | 480 |
| ggctattggc | cattgcatac | gttgtatcca | tatcataata | tgtacattta | tattggctca | 540 |
| tgtccaacat | taccgccatg | ttgacattga | ttattgacta | gttattaata | gtaatcaatt | 600 |
| acggggtcat | tagttcatag | cccatatatg | gagttccgcg | ttacataact | tacggtaaat | 660 |
| ggcccgcctg | gctgaccgcc | caacgacccc | cgcccattga | cgtcaataat | gacgtatgtt | 720 |
| cccatagtaa | cgccaatagg | gactttccat | tgacgtcaat | gggtggagta | tttacgtaa | 780 |
| actgcccact | tggcagtaca | tcaagtgtat | catatgccaa | gtacgccccc | tattgacgtc | 840 |
| aatgacggta | aatggcccgc | ctggcattat | gcccagtaca | tgaccttatg | ggactttcct | 900 |
| acttggcagt | acatctacgt | attagtcatc | gctattacca | tggtgatgcg | gttttggcag | 960 |
| tacatcaatg | ggcgtggata | gcggtttgac | tcacggggat | ttccaagtct | ccacccccatt | 1020 |
| gacgtcaatg | ggagtttgtt | ttggcaccaa | aatcaacggg | actttccaaa | atgtcgtaac | 1080 |
| aactccgccc | cattgacgca | aatgggcggt | aggcgtgtac | ggtgggaggt | ctatataagc | 1140 |
| agagctcgtt | tagtgaaccg | tcagatcgcc | tggagacgcc | atccacgctg | ttttgacctc | 1200 |
| catagaagac | accgggaccg | atccagcctc | cgcggccggg | aacggtgcat | tggaacgcgg | 1260 |
| attccccgtg | ccaagagtga | cgtaagtacc | gcctatagag | tctataggcc | caccccttg | 1320 |
| gcttcttatg | catgctatac | tgttttttggc | ttggggtcta | tacaccccccg | cttcctcatg | 1380 |
| ttataggtga | tggtatagct | tagcctatag | gtgtgggtta | ttgaccatta | ttgaccactc | 1440 |
| ccctattggt | gacgatactt | tccattacta | atccataaca | tggctctttg | ccacaactct | 1500 |
| ctttattggc | tatatgccaa | tacactgtcc | ttcagagact | gacacggact | ctgtatttt | 1560 |
| acaggatggg | gtctcattta | ttatttacaa | attcacatat | acaacaccac | cgtccccagt | 1620 |
| gccccgcagtt | tttattaaac | ataacgtggg | atctccacgc | gaatctcggg | tacgtgttcc | 1680 |
| ggacatgggc | tcttctccgg | tagcggcgga | gcttctacat | ccgagccctg | ctcccatgcc | 1740 |
| tccagcgact | catggtcgct | cggcagctcc | ttgctcctaa | cagtggaggc | cagacttagg | 1800 |
| cacagcacga | tgcccaccac | caccagtgtg | ccgcacaagg | ccgtggcggt | agggtatgtg | 1860 |
| tctgaaaatg | agctcgggga | gcgggcttgc | accgctgacg | catttggaag | acttaaggca | 1920 |
| gcggcagaag | aagatgcagg | cagctgagtt | gttgtgttct | gataagagtc | agaggtaact | 1980 |
| cccgttgcgg | tgctgttaac | ggtggagggc | agtgtagtct | gagcagtact | cgttgctgcc | 2040 |
| gcgcgcgcca | ccagacataa | tagctgacag | actaacagac | tgttcctttc | catgggtctt | 2100 |
| ttctgcagtc | accgtccttg | acacg | | | | 2125 |

<210> SEQ ID NO 2
<211> LENGTH: 16
<212> TYPE: DNA
<213> ORGANISM: Artificial Sequence
<220> FEATURE:
<223> OTHER INFORMATION: Synthetic

<400> SEQUENCE: 2
gtgtcaagga cggtga                                                    16

<210> SEQ ID NO 3
<211> LENGTH: 1144
<212> TYPE: DNA
<213> ORGANISM: Artificial Sequence
<220> FEATURE:
<223> OTHER INFORMATION: Synthetic

<400> SEQUENCE: 3
ctgcagtgaa taataaaatg tgtgtttgtc cgaaatacgc gttttgagat ttctgtcgcc     60
gactaaattc atgtcgcgcg atagtggtgt ttatcgccga tagagatggc gatattggaa    120
aaatcgatat ttgaaaatat ggcatattga aaatgtcgcc gatgtgagtt tctgtgtaac    180
tgatatcgcc attttccaa aagtgatttt tgggcatacg cgatatctgg cgatagcggc     240
ttatatcgtt tacggggat ggcgatagac gactttggtg acttgggcga ttctgtgtgt     300
cgcaaatatc gcagtttcga taggtgac agacgatatg aggctatatc gccgatagag      360
gcgacatcaa gctggcacat ggccaatgca tatcgatcta cattgaat caatattggc      420 cattagccat attattcatt ggttatatag cataaatcaa tattggctat tggccattgc    480
atacgttgta tccatatcat aatatgtaca tttatattgg ctcatgtcca acattaccgc    540
catgttgaca ttgattattg actagttatt aatagtaatc aattacgggg tcattagttc    600
atagcccata tatggagttc cgcgttacat aacttacggt aaatggcccg cctggctgac    660
cgcccaacga ccccgccca ttgacgtcaa taatgacgta tgttcccata gtaacgccaa     720
tagggacttt ccattgacgt caatgggtgg agtatttacg gtaaactgcc cacttggcag    780
tacatcaagt gtatcatatg ccaagtacgc cccctattga cgtcaatgac ggtaaatggc    840
ccgcctggca ttatgcccag tacatgacct tatgggactt tcctacttgg cagtacatct    900
acgtattagt catcgctatt accatggtga tgcggttttg gcagtacatc aatgggcgtg    960
gatagcggtt tgactcacgg ggatttccaa gtctccaccc cattgacgtc aatgggagtt   1020
tgttttggca ccaaaatcaa cgggactttc caaaatgtcg taacaactcc gccccattga   1080
cgcaaatggg cggtaggcgt gtacggtggg aggtctatat aagcagagct cgtttagtga   1140
accg                                                                1144

<210> SEQ ID NO 4
<211> LENGTH: 121
<212> TYPE: DNA
<213> ORGANISM: Artificial Sequence
<220> FEATURE:
<223> OTHER INFORMATION: Synthetic

<400> SEQUENCE: 4
tcagatcgcc tggagacgcc atccacgctg ttttgacctc catagaagac accgggaccg     60
atccagcctc cgcggccggg aacggtgcat tggaacgcgg attccccgtg ccaagagtga    120
c                                                                    121

<210> SEQ ID NO 5
<211> LENGTH: 827
<212> TYPE: DNA
<213> ORGANISM: Artificial Sequence
<220> FEATURE:
<223> OTHER INFORMATION: Synthetic

<400> SEQUENCE: 5

```
gtaagtaccg cctatagagt ctataggccc acccccttgg cttcttatgc atgctatact      60
gtttttggct tggggtctat acacccccgc ttcctcatgt tataggtgat ggtatagctt     120
agcctatagg tgtgggttat tgaccattat tgaccactcc cctattggtg acgatacttt     180
ccattactaa tccataacat ggctctttgc cacaactctc tttattggct atatgccaat     240
acactgtcct tcagagactg acacggactc tgtattttta caggatgggg tctcatttat     300
tatttacaaa ttcacatata caacaccacc gtccccagtg cccgcagttt ttattaaaca     360
taacgtggga tctccacgcg aatctcgggt acgtgttccg gacatgggct cttctccggt     420
agcggcggag cttctacatc cgagccctgc tcccatgcct ccagcgactc atggtcgctc     480
ggcagctcct tgctcctaac agtggaggcc agacttaggc acagcacgat gcccaccacc     540
accagtgtgc cgcacaaggc cgtggcggta gggtatgtgt ctgaaaatga gctcggggag     600
cgggcttgca ccgctgacgc atttggaaga cttaaggcag cggcagaaga agatgcaggc     660
agctgagttg ttgtgttctg ataagagtca gaggtaactc ccgttgcggt gctgttaacg     720
gtggagggca gtgtagtctg agcagtactc gttgctgccg cgcgcgccac cagacataat     780
agctgacaga ctaacagact gttcctttcc atgggtcttt tctgcag                   827
```

<210> SEQ ID NO 6
<211> LENGTH: 17
<212> TYPE: DNA
<213> ORGANISM: Artificial Sequence
<220> FEATURE:
<223> OTHER INFORMATION: Synthetic

<400> SEQUENCE: 6

```
tcaccgtcct tgacacg                                                     17
```

<210> SEQ ID NO 7
<211> LENGTH: 592
<212> TYPE: DNA
<213> ORGANISM: Artificial Sequence
<220> FEATURE:
<223> OTHER INFORMATION: Synthetic

<400> SEQUENCE: 7

```
aatcaacctc tggattacaa aatttgtgaa agattgactg atattcttaa ctatgttgct      60
ccttttacgc tgtgtggata tgctgcttta atgcctctgt atcatgctat gcttcccgt      120 acggctttcg ttttctcctc cttgtataaa tcctggttgc tgtctcttta tgaggagttg     180
tggcccgttg tccgtcaacg tggcgtggtg tgctctgtgt ttgctgacgc aaccccact      240 ggctggggca ttgccaccac ctgtcaactc ctttctggga ctttcgcttt ccccctcccg     300
atcgccacgg cagaactcat cgccgcctgc cttgcccgct gctggacagg ggctaggttg     360
ctgggcactg ataattccgt ggtgttgtcg gggaagctga cgtcctttcc atggctgctc     420
gcctgtgttg ccaactggat cctgcgcggg acgtccttct gctacgtccc ttcggctctc     480
```

```
aatccagcgg acctcccttc ccgaggcctt ctgccggttc tgcggcctct cccgcgtctt    540
cgctttcggc ctccgacgag tcggatctcc ctttgggccg cctccccgcc tg           592
```